United States Patent [19]
Narh et al.

[11] Patent Number: 6,142,662
[45] Date of Patent: Nov. 7, 2000

[54] APPARATUS AND METHOD FOR SIMULTANEOUSLY DETERMINING THERMAL CONDUCTIVITY AND THERMAL CONTACT RESISTANCE

[75] Inventors: Kwabena A. Narh, Wayne; L. Sridhar, Palisades Park, both of N.J.

[73] Assignee: New Jersey Institute of Technology, Newark, N.J.

[21] Appl. No.: 09/098,630

[22] Filed: Jun. 16, 1998

[51] Int. Cl.[7] ........................... G01N 25/18; G01N 25/00; G01N 25/20

[52] U.S. Cl. ................... 374/44; 374/43; 374/30; 374/29

[58] Field of Search .................. 374/10, 29, 30, 374/43, 44

[56] References Cited

U.S. PATENT DOCUMENTS

| | | |
|---|---|---|
| 3,592,060 | 7/1971 | Laverman . |
| 3,733,887 | 5/1973 | Stanley et al. ........................... 374/44 |
| 4,630,938 | 12/1986 | Piorkowska-Palczewska et al. . |
| 4,861,167 | 8/1989 | Lobo et al. ............................. 374/44 |
| 4,929,089 | 5/1990 | Tsuchida . |
| 5,005,985 | 4/1991 | Piorkowska-Galeska et al. ....... 374/29 |
| 5,112,136 | 5/1992 | Sakuma et al. . |
| 5,233,308 | 8/1993 | Willis . |
| 5,258,929 | 11/1993 | Tsuchida . |
| 5,297,868 | 3/1994 | Graebner . |
| 5,713,665 | 2/1998 | Kato et al. . |
| 5,940,784 | 8/1999 | El-Husayni ............................. 374/43 |
| 5,997,174 | 12/1999 | Wyland ................................... 374/43 |

FOREIGN PATENT DOCUMENTS

| | | |
|---|---|---|
| 325430 | 7/1989 | European Pat. Off. . |
| 347571 | 12/1989 | European Pat. Off. . |
| 644418 | 3/1995 | European Pat. Off. . |
| 56-061640 | 5/1981 | Japan . |
| 56-087850 | 7/1981 | Japan . |
| 57-138758 | 8/1982 | Japan . |
| 5028094 | 2/1993 | Japan . |
| 5064187 | 3/1993 | Japan . |
| 5312741 | 11/1993 | Japan . |
| 6272004 | 9/1994 | Japan . |
| 7134108 | 5/1995 | Japan . |

OTHER PUBLICATIONS

Beck et al., 1974, Parameter Estimation in Engineering and Science, John Wiley, new York.
Dulikravich et al., 1997, Inverse Problems and Optimization in Heat Conduction, Taylor and Francis, Washington, DC.
Fletcher, Nov. 1988, J Heat Transfer, 110:1059–80.
Holman et al., 1984, Experimental Methods for Engineers, McGraw Hill, New York.
Jurkowski et al., ICHEME Symposium Series, No. 129 (No Date).
Lobo et al., Jan. 1990, Polymer Engg and Sci, 30:65–9.
Lobo et al., 1990, SPE–ANTEC, 90:862–5.
Mohr et al., May 1997, J Heat Transfer, 119:363–6.
Moses et al., 1989, J Thermophysics, 3:474–6.
Narh et al., 1997, ANTEC'97, Toronto, Canada, 2273–7.
Peterson et al., Nov. 1988, J Heat Transfer, 110:996–9.
Rhee et al., 1993, SPE–ANTEC'3.
Yu et al., Dec. 1990, Polymer Engg and Sci, 30:1599–605.

*Primary Examiner*—Diego Gutierrez
*Assistant Examiner*—Jeanne Marguerite Goodwin
*Attorney, Agent, or Firm*—Klauber & Jackson

[57] ABSTRACT

An apparatus and method for simultaneously determining thermal conductivity and thermal contact resistance of a sample which employs an transient method of taking data for use in such determinations, and an inverse method of determining the values using a methodology set forth herein. As a result, the present invention permits a more accurate, and economically efficient determination of thermal conductivity and thermal contact resistance than methods presently used.

57 Claims, 14 Drawing Sheets

Flowchart for the heat transfer calculation:

APPARATUS AND METHOD FOR SIMULTANEOUSLY DETERMINING THERMAL CONDUCTIVITY AND THERMAL CONTACT RESISTANCE

FIELD OF THE INVENTION

Broadly, the present invention involves an apparatus and method for simultaneously determining thermal conductivity of a sample, and the thermal contact resistance of the sample at an interface with another material.

BACKGROUND OF THE INVENTION

Properties affecting thermal transport are important parameters in the simulation of plastic processing techniques such as injection molding, thermoforming, or extrusion, to name only a few such techniques. In order to simulate such processes as accurately as possible, and hence, ultimately improve the productivity of manufacturing plants utilizing these processes, it is important to determine these parameters as accurately as possible. An example of the importance of the accuracy of these parameters was shown in a study wherein it was determined that in high volume manufacturing processes such as injection molding, a small cycle time reduction based on a more accurate simulation could result in substantial improvement in productivity [Lobo, H. And Newman, R. (1990) *Thermal Conductivity of Polymers at High Temperatures and Pressures*" SPE-ANTEC'90, 862–865, which is hereby incorporated by reference in its entirety].

In the process of injection molding, the thermal conductivity of polymers and the thermal contact resistance at the polymer-metal interface are two important parameters that govern the heat flow from the molten polymer. Generally, thermal conductivity measurements of polymers are performed using both steady state and transient methods, while thermal contact resistance measurements are conducted by steady state methods. A steady state method generally involves heating a sample to a constant temperature, and then taking data on the temperature of a specific material surrounding the sample at a specific distance from the interface of the sample and the material. These data can then be used to calculate thermal conductivity. In a transient method, the temperature of a material surrounding the sample is taken as a function of time while the temperature of the sample either increases or decreases. Examples of steady state methods presently used to determine the thermal conductivity of a sample include the guarded hot plate method, and methods using heat flux meters [Holman, J. P., and Gadja, W. J. (1984). *Experimental Methods for Engineers*. McGraw Hill, New York, which is hereby incorporated by reference in its entirety].

Further, examples of transient techniques used to determine thermal conductivity include, but are not limited to the line source method for determining thermal conductivity of polymers (Lobo and Cohen, 1990).

As explained above, experimental methods for determining thermal contact resistance are generally performed using steady state methods (Mohr, J. W., Seyed-Yagoobi, J., and Price D. C. (1997). "Thermal Contact conductance at a Paper/Elastomer Interface." *Journal of Heat Transfer,* 119, 363–366; Narh, K. A., and Sridhar, L. "Measurement and Modeling of Thermal Contact Resistance at a Plastic Metal Interface." ANTEC '97, Toronto, Canada, 2273–2277; which are hereby incorporated by reference in their entireties] or a quasi-steady state method [Moses, W. M., and Johnson, R. R. (1989). "Experimental Results for the Quasi steady Heat Transfer Through Periodically Contacting Surfaces." *J. Thermophysics,* 3(4):474–476, which is hereby incorporated by reference herein in its entirety] using temperature measurements, taken at a predetermined distance from the interface, to extrapolate to the interface temperatures, and to calculate the heat flux crossing the interface.

However, steady-state methods of determining thermal heat conductivity contain inherent limitations. Initially, they are very time consuming in that the sample must initially be brought to a steady state prior to determining its thermal conductivity or thermal contact resistance. Moreover, the surfaces of the sample must be "conditioned" prior to determining the thermal conductivity. Conditioning the sample involves keeping the sample at the desired constant temperature for a period of time, usually at least 25 minutes prior to bringing the sample to the steady state temperature. This procedure prepares the surfaces of the sample for determining the thermal conductivity of the sample.

Another drawback in the use of steady state methods to determine the thermal contact resistance is that it does not permit the determination of such resistances at two interfaces, i.e. where opposite surfaces of a sample contact the surface of a second material. Rather, calculations used in steady state methods inherently provide only the average thermal contact resistance of both surfaces of the sample.

Another limitation of steady state methods for determining thermal conductivity or thermal contact resistance involves changes in the physical shape of the sample as a result of heating, which can alter or skew thermal conductivity or thermal contact resistance measurements. In particular, it as been concluded that thermal contact resistance at an elastomer-elastomer interface depends on the flatness rather than on microscopic asperities of the surface of the sample (Mohr et al. 1997). Hence at lower contact pressures of the interface, deviation from the surface flatness causes much larger interfacial gaps, and hence, larger thermal conductivity values than those due to microscopic asperities, which can result in an inaccurate determination of such values.

Hence, what is needed is a transient method of determining thermal conductivity and thermal contact resistance of a sample at an interface with another material, and hence accurately determine thermal contact resistance and thermal conductivity in an efficient and economical manner.

What is further needed is an approach to calculating thermal contact resistance and thermal conductivity which permits the simultaneous determination of these values.

The citation of any reference herein should not be construed as an admission that such reference is available as "Prior Art" to the instant application.

SUMMARY OF THE INVENTION

There is provided, in accordance with the present invention, an apparatus and method for simultaneously determining the thermal conductivity and thermal contact resistance for a particular sample that does not possess the shortcomings of the methods explained above, and offers the advantage of being quicker, and more accurate than such methods.

Broadly, the present invention extends to an apparatus for simultaneously determining the thermal conductivity and thermal contact resistance of a sample, wherein the sample defines a first and second surface. An example of an apparatus of the present invention comprises a first block comprising an upper surface, a lower surface, and a periphery, and a second block comprising an upper surface, a lower surface, and a periphery, wherein the first and second blocks comprise a melting point greater than that of the sample. Furthermore, an apparatus of the invention comprises a sample chamber for holding the sample, wherein the chamber is defined by the lower surface of the second block and the upper surface of the first block. As a result, when a sample is placed into the sample chamber, two interfaces are formed between the sample and the apparatus, i.e., a first interface is formed between the first surface of the sample and the lower surface of the second block, and a second interface is formed between the second surface of the sample and the upper surface of the first block. An apparatus of the present invention also comprises a means for modulating the temperature of the sample in the sample chamber, a means for measuring the temperature of the first block and the second block as a function of time while the temperature of the sample is being modulated, and a computing means interfaced with the temperature measuring means, wherein the computing means simultaneously determines the thermal conductivity of the sample and the thermal contact resistance of the sample at the first and second interfaces using the temperatures measured for the first block and the second block as a function of time, wherein the computing means utilizes the function of:
where:

C is heat capacity (j/m$^3$–K), k is thermal conductivity (W/m–K), $R_c$ is thermal contact resistance (m$^2$–K/W), n,m are number of points at which k and $R_c$ are defined, respectively, t is time (seconds), T is Temperature, vector of measured temperature (C), V is variance matrix, W is weighting matrix, x is axial distance (m), X is sensitivity matrix=$[\partial \eta_i / \partial \beta_j]$, β is parameter vector=$[k_{t=1,n} \ R_{c1}|_{t=1,n} \ R_{c2}|_{t=1,n}]^T$, η is Temperature, vector of temperatures from physical model of apparatus (°C.), ν is initial value of β, $R_S$ is the thermal resistance of the sample=t/kA(m$^2$–K/W), $t_h$ is sample thickness (m)

A is surface area (m$^2$),
subscripts

1,2 are upper and lower interfaces between plastic specimen and steel blocks, respectively.

$$\beta_{k+1}=\beta_k+[X^TWX+V]^{-1}[X^TW(T-\eta(\beta_k))+V(\nu-\beta_k)] \quad (1)$$

which relates temperature, time, thermal conductivity, thermal contact resistance at the two interfaces, and pressure of the sample.

Moreover, the present invention extends to an apparatus for simultaneously determining thermal conductivity and thermal contact resistance of a sample, as set forth above, wherein the first and second blocks are comprised of a material that conducts heat. Examples of materials having applications as blocks in an apparatus of the invention include, but are not limited to metals, such as copper, steel, gold, or aluminum, to name just a few, or polymers such as TEFLON, having melting points greater than the melting point of a sample being tested. In a preferred embodiment, the blocks of an apparatus of the invention are cylindrically shaped and comprised of mold steel.

Furthermore, the present invention extends to an apparatus for simultaneously determining thermal conductivity and thermal contact resistance of a sample as set forth above, wherein the temperature modulating means comprises a heat source connected to the upper surface of the second block, and a heat sink connected to the lower surface of the first block, such that the heat sink has a temperature less than the temperature of the heat source, and heat propagates in a one dimensional direction from the heat source, through the second block, the sample in the sample chamber, and then through the first block, to the heat sink. In an alternative embodiment, the heat source is connected to the lower surface of the first block, and generates heat which is conducted in a one dimensional direction from the heat source, through the first block, conducted to the sample in the sample chamber, conducted from the sample to the second block, and then eventually absorbed by a heat sink connected to the upper surface of the second block. In either embodiment, heat is conducted in a one dimensional direction from the heat source to the heat sink. Numerous heat sources having applications in an apparatus of the invention are presently available to the skilled artisan. Examples of such heat sources include, but are not limited to means for generating a beam of electromagnetic radiation and focusing the beam onto the upper surface of the second block, or the lower surface of the first block, depending upon the embodiment of the apparatus used, an electrical heater which undergoes joule heating which is connected to either the upper surface of the second block or the lower surface of the first block, depending upon the embodiment used, or a combustion means, i.e., burning an inflammable material, such as alkane or alcohol at either the upper surface of the second block or the lower surface of the first block, to produce heat. Preferably, the heat source of an apparatus of the present invention is an electrical heater which undergoes joule heating.

The present invention further extends to an apparatus for simultaneously determining thermal conductivity and thermal contact resistance as set forth herein, wherein the heat sink is connected to either the lower surface of the first block or the upper surface of the second block, depending on the embodiment of the invention. The heat sink of the present invention has a temperature lower than that of the heat source. Numerous examples of heat sinks have applications in the present invention. In a particular example, the heat sink comprises a coiled metal tube surrounded with a copper jacket, wherein the coiled metal tube contains a constant temperature bath of circulating heat transfer oil. However, equivalent heat sinks are readily apparent to the skilled artisan and are also encompassed by the present invention.

The present invention further extends to an apparatus as described above, wherein the temperature measuring means described above comprises a temperature sensing means connected to the blocks, and a temperature calculating means connected to the temperature sensing means, such that the calculating means converts a signal from the temperature sensing means into a numerical temperature value. Examples of temperature sensing means connected to the blocks, and having applications in the present invention include a thermocouple, a thermometer, or a fiber optic fluorescence based temperature sensor.

Moreover, numerous temperature calculating means connected to a temperature sensing means of the invention have applications in the present invention and include, but are not limited to a computer comprising a data acquisition system, which comprises an isothermal terminal block, multiplexer/signal conditioner and data acquisition board, for converting signals received from the temperature sensing means into a numerical temperature value.

In addition, the present invention extends to an apparatus for simultaneously determining thermal conductivity and thermal contact resistance of a sample, as described above, wherein the first and second blocks further comprise at least two bores from a center axis of the blocks to their respective peripheries. Such bores are parallel to the upper and lower surfaces of the respective blocks, and are located at specific locations, or nodes, relative to the first and second interfaces of the sample in the sample chamber and the blocks. The temperature sensing means as described above are inserted into these bores such that they make contact with the block at their central axes. In a particular embodiment of the invention, the temperature sensing means comprises a J-type thermocouple inserted into these bores such that the tip of the thermocouple in each bore contacts a respective block at its central axis. Furthermore, the temperature calculating means of this particular embodiment of the invention is connected to the thermocouples, and comprises a computer having a data acquisition system comprising an isothermal terminal block, multiplexer/signal condition and data acquisition board, such that the calculating means converts signals received from the thermocouples into a numerical temperature value. Optionally, the blocks are surrounded with an insulating material such as STYROFOAM or fiberglass, to name only a few, so that heat produced by the heat source is not lost to the surroundings, but travels in a one dimensional direction to the heat sink.

Furthermore, the present invention extends to an apparatus for simultaneously determining the thermal conductivity and thermal contact resistance of a sample, as set forth above, wherein the computing means for determining thermal conductivity and thermal contact resistance as set forth above, comprises a computer programmed to solve the function set forth below:

$$\beta_{k+1}=\beta_k+[X^TWX+V]^{-1}[X^TW(T-\eta(\beta_k))+V(v-\beta_k)] \quad (1)$$

using a methodology set forth in the flow chart of FIGS. 12a and 12b. Numerous methods of programming a computer to solve this function are readily apparent and available to the skilled artisan, and are not described in detail here.

Optionally, an apparatus of the present invention may further comprise a pressure modulating means for modulating the pressure under which the sample is held in the sample chamber. Since pressure is a parameter of Eq. (1), one can change the pressure on the sample and calculate the thermal conductivity of the sample and the thermal contact resistance at the first and second interfaces of the sample as a function of the pressure on the sample. An example of a means for modulating the pressure of the sample in the sample chamber comprises a means of translating one of the blocks towards the other block such that the lower surface of the second block remains parallel to the upper surface of the first block. As a result, the pressure or load upon the sample in the sample chamber can be increased and maintained on the sample while temperature data is taken. Numerous translating means are presently available to the skilled artisan, and have applications in the present invention. For example, hydraulic or pneumatic pressure, such as that used in a hydraulic press can be used to translate the second block towards the first block, and hence increase the pressure on the sample. Other methods involve a system of pulleys and weights, and a manual press. In a particular embodiment, the means of modulating the pressure or load upon the sample comprises a means for translating the second block relative to the position of the first block. Such a translating means comprises a frame surrounding the apparatus, wherein the frame comprising an upper plate having an internally threaded bore, and a lower plate connected to at least two guide rods which are perpendicular to the lower plate, wherein the guide rods are positioned such that the first block, the second block, and the temperature modulating means are located between the guide rods, a plate connected to the upper surface of the second block, wherein the plate comprises at least two holes therethrough so that the guide rods can pass through the plate, and an externally threaded rotatable shaft having an upper end and a lower end, wherein the shaft engages the internally threaded bore, and the lower end of the shaft contacts the plate, such that when the shaft is rotated, the second block is translated towards the first block, the volume of the sample chamber decreases, and pressure upon the sample in the sample chamber increases.

In another embodiment, the present invention extends to an apparatus for simultaneously determining the thermal conductivity and thermal contact resistance of a sample, wherein the sample defines a first and second surface, wherein an apparatus of the present invention comprises a first block comprising an upper surface, a lower surface, and a periphery, wherein the first block comprises a melting point greater than the melting point of the sample, and a second block comprising an upper surface, a lower surface, and a periphery, wherein the second block comprises a melting point greater than the melting point of the sample. Furthermore, an apparatus of the invention comprises a sample chamber for holding the sample, wherein the chamber is defined by the lower surface of the second block and the upper surface of the first block. As a result, when a sample is placed into the sample chamber, two interfaces are formed between the sample and the apparatus, i.e., a first interface is formed between the first surface of the sample and the lower surface of the second block, and a second interface is formed between the second surface of the sample and the upper surface of the first block. An apparatus of the present invention also comprises a heat source connected to the upper surface of the second block, and a heat sink connected to the lower surface of the first block, such that the temperature of the heat sink is less than the temperature of the heat source. Alternatively, the heat source of an apparatus of the invention may be connected to the lower surface of the first block, and the heat sink can be connected to the upper surface of the second block. Hence, in either example, energy in the form of heat produced by the heat source propagates through the block connected to the heat source to the sample in the sample chamber. Heat then propagates through the sample to the block connected to the heat sink, and ultimately propagates through that block and is collected in the heat sink. In addition, an apparatus of the invention comprises a means for sensing the temperature of the first block and the second block as a function of time, a temperature calculating means connected to the temperature sensing means to convert signals from the temperature sensing means into a numerical temperature values as a function of time, and a computing means interfaced with the temperature calculating means, wherein the computing means simultaneously determines the thermal conductivity of the sample and the thermal contact resistance of the sample at the first and second interfaces using the temperatures calculated for the first block and the second block as a function of time, wherein the computing means utilizes the function of:

$$\beta_{k+1}=\beta_k+[X^TWX+V]^{-1}[X^TW(T-\eta(\beta_k))+V(v-\beta_k)] \quad (1)$$

which relates temperature, time, thermal conductivity, thermal contact resistance at the two interfaces, and pressure of the sample.

Moreover, the present invention extends to an apparatus for simultaneously determining thermal conductivity and thermal contact resistance of a sample, as set forth above, wherein the first and second blocks are comprised of a material that conducts heat so that heat can propagate in a one dimensional fashion from the heat source through the block connected thereto, the sample, and the block connected to the heat sink. Examples of materials having applications as blocks in an apparatus of the invention include, but are not limited to metals, such as copper, steel, gold, or aluminum, to name just a few, or polymers such as TEFLON, having melting points greater than the melting point of a sample being tested. In a preferred embodiment, the blocks of an apparatus of the invention are cylindrically shaped and comprised of mold steel.

Furthermore, the present invention extends to an apparatus for simultaneously determining thermal conductivity and thermal contact resistance of a sample, wherein the heat source connected to the upper surface of the second block can generate heat which propagates in a one dimensional direction from the heat source to the heat sink. Hence, in one embodiment of the invention heat produced by the heat source is absorbed by the second block, conducted to the sample via the first interface, conducted from the sample to the first block via the second interface, and then eventually absorbed by the heat sink connected to the lower surface of the first block. In an alternative embodiment, the heat source is connected to the lower surface of the first block and the heat sink is connected to the upper surface of the second block. Heat generated by the heat source is absorbed by the first block, conducted to the sample via the second interface, conducted from the sample to the second block via the first interface, and then eventually absorbed by the heat sink connected to the upper surface of the second block. In either embodiment, heat produced by the heat source propagates in a one dimensional direction to the heat sink. Numerous heat sources having applications in an apparatus of the invention are presently available to the skilled artisan. Examples of such heat sources include, but are not limited to means for generating a beam of electromagnetic radiation and focusing the beam onto the upper surface of the second block, or the lower surface of the first block, depending upon the embodiment of the apparatus used, an electrical heater which undergoes joule heating, or a combustion means, i.e., burning an inflammable material, such as alkane or alcohol, to produce heat. In a particular embodiment, the heat source of an apparatus of the present invention is an electrical heater which undergoes joule heating.

The present invention further extends to an apparatus for simultaneously determining thermal conductivity and thermal contact resistance as set forth herein, wherein the heat sink connected to either the lower surface of the first block or the upper surface of the second block, depending on the embodiment of the invention, is capable of absorbing heat conducted through the first block, and has a temperature lower than that of the heat source. Numerous examples of heat sinks have applications in the present invention. In a particular example, the heat sink comprises a coiled metal tube surrounded with a copper jacket, wherein the coiled metal tube contains a constant temperature bath of circulating heat transfer oil.

In addition, the present invention extends to an apparatus for simultaneously determining thermal conductivity and thermal contact resistance of a sample, as described above, wherein the temperature sensing means of an apparatus of the invention comprises a thermometer, a thermocouple, or a fiber optic fluorescence based temperature sensor connected to the first and second blocks. Moreover, a temperature calculating means is connected to a temperature sensing means of the invention. Numerous temperature calculating means are presently available and have applications in the present invention. In a particular example, a temperature calculating means comprises a computer having a data acquisition system comprising an isothermal block, multiplexer/signal condition and data acquisition board, for converting signals received from the temperature sensing means connected to the blocks into a numerical temperature value.

Futhermore, the present invention further extends to an apparatus as described above, wherein the first and second blocks further comprise at least two bores, wherein the bores extend from the periphery of the blocks to a central axis of the blocks, are parallel to the upper and lower surfaces of the blocks, and are located at specific nodes or locations relative to the first and second interfaces formed by the sample in the sample chamber and the blocks. The temperature sensing means connected to the blocks are inserted into the bores and contacts the blocks at their central axis, providing an accurate sensing of the temperature of the blocks as a function of time. Examples of temperature sensing means having applications in the present invention include, but are not limited to, a thermometer inserted into the bores, a fiber optic fluorescence based temperature sensor inserted into the bores, or a thermocouple inserted into the bores. Preferably, the temperature sensing means comprises a J-type thermocouple inserted into the at least two bores of the of the first and second blocks until the tips of the thermocouples make contact with the central axis of respective blocks. Furthermore, a thermal conductivity paste is may also be inserted into the bores to ensure good contact between the tip of the thermocouples and the blocks. An example of a temperature calculating means connected to the thermocouples for converting signals from the thermocouples into numerical temperature values includes, but is not limited to a computer comprising a data acquisition system having an isothermal terminal block, multiplexer/signal conditioner and a data acquisition board.

Furthermore, the present invention extends to an apparatus for simultaneously determining the thermal conductivity and thermal contact resistance of a sample, as set forth above, wherein the computing means for determining thermal conductivity and thermal contact resistance as set forth above, is a computer programmed to solve the function set forth below:

$$\beta_{k+1} = \beta_k + [X^T W X + V]^{-1} [X^T W (T - \eta(\beta_k)) + V(v - \beta_k)] \qquad (1)$$

using a methodology set forth in the flow chart of FIGS. 12a and 12b. Numerous methods of programming a computer to solve this function are readily apparent and available to the skilled artisan, and are not described in detail here.

Optionally, an apparatus of the present invention may further comprise a pressure modulating means for modulating the pressure under which the sample is held in the sample chamber. Since pressure is a parameter of Eq. (1), one can change the pressure on the sample and calculate the thermal conductivity of the sample and the thermal contact resistance at the first and second interfaces of the sample as a function of the pressure on the sample. An example of a means for modulating the pressure of the sample in the sample chamber comprises a means of translating one of the blocks towards the other block in such a manner that the lower surface of the second block remains parallel to the upper surface of the first block. As a result, the pressure or load upon the sample in the sample chamber can be increased and maintained while temperature data is taken. Numerous translating means are presently available to the skilled artisan, and have applications in the present invention. For example, hydraulic or pneumatic pressure, such as that used in a hydraulic press, can be used to translate the second block relative to the first block, and hence increase the pressure on the sample. Other methods involve a system of pulleys and weights, or a mechanical press. In a particular embodiment, the means of modulating the pressure on the sample in the sample chamber comprises a means for translating the second block relative to the position of the first block, wherein the translating means comprises a frame comprising an upper plate having an internally threaded bore, and a lower plate connected to at least two guide rods which are perpendicular to the lower plate. The at least two guide rods are positioned such that the heat sink, the first block, the second block, the sample chamber and the heat source of the apparatus of the invention are located between the guide rods. Furthermore, the translating means comprises a plate connected to the heat source such that the heat source is located between the plate and the second block, wherein the plate comprises at least two holes so that the guide rods can pass through the plate, and an externally threaded rotatable shaft having an upper end and a lower end, wherein the shaft engages the internally threaded bore, and the lower end of the shaft is in contact with the plate. As a result, when the shaft is rotated, the second block is translated towards the first block, the volume of the sample chamber decreases, and the pressure upon the sample in the sample chamber increases.

In addition, the present invention extends to a method for simultaneously determining the thermal conductivity and thermal contact resistance of a sample, wherein the sample defines a first and second surface. Such a method comprises the steps of providing a first block comprising an upper surface, a lower surface and a periphery, and a second block comprising an upper surface, a lower surface and a periphery, wherein the blocks comprise a melting point greater than that of the sample. Further, a method of the invention comprises forming a sample chamber for holding the sample, wherein the chamber is formed by positioning the first and second blocks so that the upper surface of the first block is parallel to the lower surface of the second block, thereby defining the sample chamber for holding the sample. As a result, when a sample is in the chamber, a first interface is formed between the first surface of the sample and the lower surface of the second block, and a second interface is formed between the second surface of the sample and the upper surface of the first block. A method of the invention further comprises modulating the temperature of the sample, measuring the temperature of the first and second blocks at two specific locations, or nodes, relative to the first and second interfaces as a function of time during the modulating of the temperature of the sample, and determining simultaneously the thermal conductivity of the sample and the thermal contact resistance of the sample at the first and second interfaces, using the temperatures of the blocks and the function:

$$\beta_{k+1}=\beta_k+[X^T W X+V]^{-1}[X^T W(T-\eta(\beta_k))+V(v-\beta_k)] \quad (1)$$

Moreover, the present invention extends to a method for simultaneously determining thermal conductivity and thermal contact resistance of a sample as set forth above, wherein the first and second blocks are comprised of a material that conducts heat. Numerous materials that conduct heat can be used in the blocks of the methods of the present invention. For example, the blocks can be made of a metal, such as copper, steel, iron, gold, or aluminum, to name only few. Moreover, blocks of the method can be comprised of a polymeric material which has a melting point greater than the melting point of the sample. A particular example of such a polymeric material is TEFLON. Preferably, the blocks are cylindrically shaped and comprised of mold steel.

The present invention further extends to a method for simultaneously determining thermal conductivity and thermal contact resistance of a sample at interfaces the sample has with other materials, wherein the step of modulating the temperature of the sample comprises connecting a heat source to the upper surface of the second block, and connecting a heat sink to the lower surface of the first block, wherein the temperature of the heat sink is less than the temperature of the heat source, and heat is conducted from the heat source, through the sample and to the heat sink in a one dimensional direction. Alternatively, the step of modulating the temperature of the sample comprises connecting a heat source to the lower surface of the first block and a heat sink to the upper surface of the second block, such that heat is conducted through the sample and to the heat sink in a one dimensional direction. Numerous heat sources are available and have applications in the present invention. For example, the heat source may comprise a beam of electromagnetic radiation focused onto either the lower surface of the first block, or the upper surface of the second block, depending upon the embodiment of the invention. If the block absorbs the radiation, it is heated, and the heat is conducted to the sample in a one dimensional direction. Other heat sources having applications herein include an electrical heater which undergoes joule heating, or combustion of an inflammable material adjacent to one of the blocks. Such an inflammable material includes, but is not limited to an alkane or an alcohol. Preferably, the heat source of the method of the invention comprises an electrical heater which undergoes joule heating.

Furthermore, numerous heat sinks having applications in the invention. An example of a heat sink having applications in the step of modulating the temperature of a sample in a sample chamber of the invention includes, but is not limited to a coiled metal tube contained in a copper jacket, wherein the tube contains a constant temperature bath of circulating oil. The heat sink is connected to either the lower surface of the first block or the upper surface of the second block, depending upon which embodiment of the invention is being used.

In addition, the present invention extends to a method for simultaneously determining the thermal conductivity and thermal contact resistance of a sample, as set forth above, wherein the step of measuring the temperature involves connecting a means of sensing temperature to the blocks, and in turn, connecting the temperature sensing means to a temperature calculating means for calculating the temperature of the blocks by converting signals received from the temperature sensing means into numerical temperature values. Examples of temperature sensing means connected to the first and second blocks having applications in a method of the invention comprise a thermometer, a thermocouple, or a fiber optic fluorescence based temperature sensor, to name only a few. Moreover, an example of a temperature calculating means connected to a temperature sensing means includes, but is not limited to a computer having a data acquisition system comprising an isothermal terminal block, multiplexer/signal conditioner and data acquisition board, for converting signals received from the temperature sensing means into numerical temperature values.

Furthermore, the present invention extends to a method for simultaneously determining thermal conductivity and thermal contact resistance of a sample, as set forth above, wherein the blocks further comprise at least two bores, wherein the bores extend from the periphery of the blocks to a central axis of the blocks, are parallel to the upper and lower surfaces of the blocks, and are located at specific nodes relative to the first and second interfaces of the sample in the sample chamber with the blocks, and the temperature sensing means is inserted into the bores and contacts the blocks at the central axis, in order to sense accurately the temperature of the block.

In a preferred embodiment, the temperature sensing means comprises a J-type thermocouple inserted into the bores, such that the tip of the thermocouple in each bore contacts the respective block at the central axis, and the temperature calculating means connected to the J-type thermocouples comprises a computer having a data acquisition system comprising an isothermal terminal block, multiplexer/signal conditioner and data acquisition board.

Moreover, the present invention extends to a method of simultaneously determining the thermal conductivity and thermal contact resistance of a sample, as described above, further comprising the step of modulating the pressure under which the sample is held and maintaining the modulated pressure on the sample prior to modulating the temperature of the sample.

Numerous methods of modulating the pressure or load upon the sample in the sample chamber are readily apparent to the skilled artisan, and are encompassed by the present invention. A particular method involves translating one of the blocks towards the other block such that the lower surface of the second block remains parallel to the upper surface of the second block. In a particular embodiment of the invention, translating one block, such as the second block, towards the first block such that the lower surface of the first block remains parallel with the upper surface of the second block comprises providing a frame comprising an upper plate having an internally threaded bore, and a lower plate connected to the at least two guide rods that are perpendicular to the lower plate, wherein the guide rods are positioned such that the first block, the second block and the sample chamber are located between the guide rods, connecting a plate to the upper surface of the second block, wherein the plate comprises at least two holes aligned with the guide rods so that the guide rods can pass through the plate, providing an externally threaded rotatable shaft having an upper end and a lower end, wherein the shaft engages the internally threaded bore, and the lower end of the shaft is in contact with the plate. As a result, when the shaft is rotated, the second block is translated towards the first block, the volume of the sample decreases, and the pressure upon the sample in the sample chamber increases.

Naturally, the present invention extends to a method for simultaneously determining thermal conductivity and thermal contact resistance of a sample as set forth herein, wherein the step of simultaneously computing the thermal conductivity and thermal contact resistance of the sample comprises entering the measured temperatures of the first and second blocks as a function of time, into a computer programmed to solve the following function:

$$\beta_{k+1}=\beta_k+[X^TWX+V]^{-1}[X^TW(T-\eta(\beta_k))+V(v-\beta_k)] \quad (1)$$

using a methodology set forth in the flow chart of FIGS. 12a and 12b. Programming a computer in this manner is readily apparent to one of ordinary skill in the art, and hence is not explained in detail here.

Accordingly, it a principal object of the present invention to provide a transient means for simultaneously determining the thermal conductivity and thermal contact resistance of a sample, such as a polymer, that is more accurate than presently used steady state methods.

It is another object of the present invention to increase the efficiency of such a determination and avoid conditioning the surfaces of a sample, and placing and maintaining the sample in a steady state condition.

It is yet another object of the present invention to permit the determination of the thermal contact resistance of a sample at two distinct interfaces with different materials rather than the average thermal contact resistance of both interfaces. As a result, the present invention provides a valuable means for simulating processes such as injection molding, and thereby provides valuable information on increasing the productivity of such processes.

It is yet another object of the present invention to provide an apparatus and method for determining thermal conductivity and thermal contact resistance of a sample, regardless of whether the temperature of the sample is increasing or decreasing, and regardless of the pressure or load placed upon the sample.

These and other aspects of the present invention will be better appreciated by reference to the following drawings and Detailed Description.

DETAILED DESCRIPTION OF THE INVENTION

Figure 1:
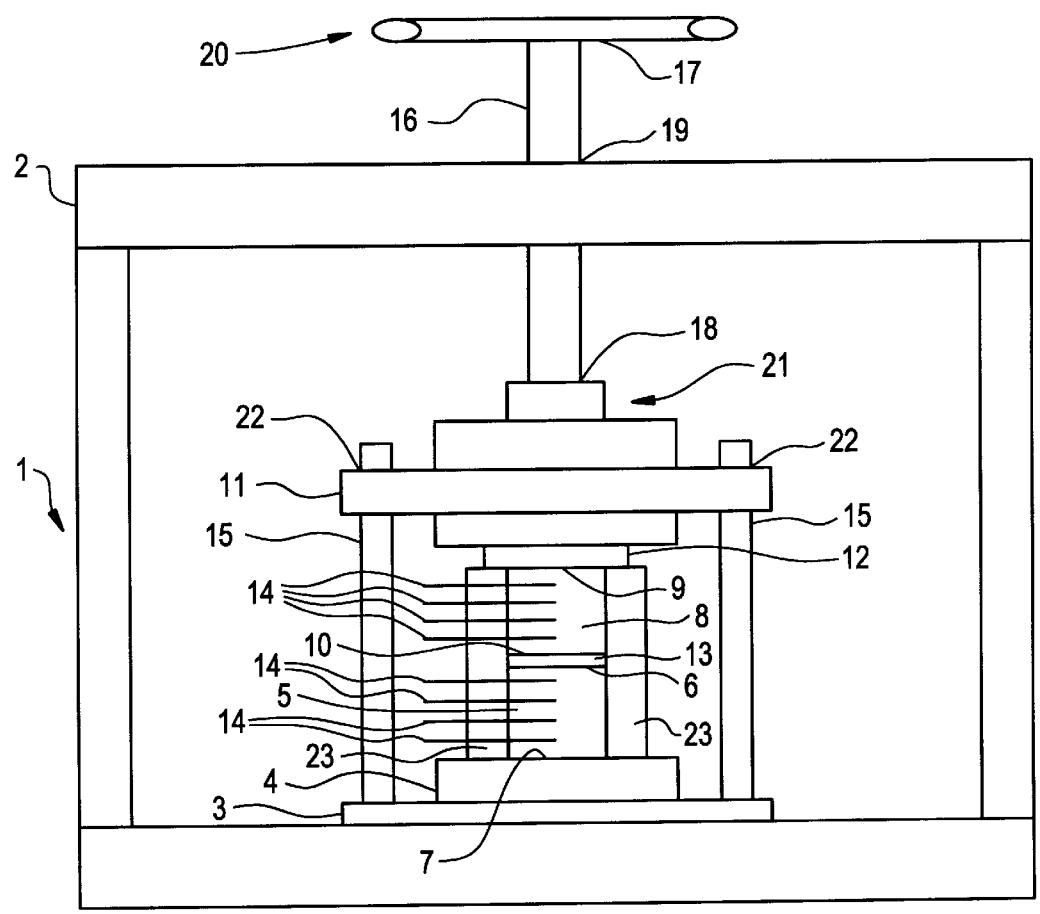
FIG. 1 is a schematical drawing of an embodiment of an apparatus of the present invention.

The invention is based upon Applicants' recognition that steady state methods for calculating thermal conductivity and thermal contact resistance are not accurate in that they do not actually simulate processes such as injection molding. In particular, Applicants have recognized that the thermal contact resistance of materials in injection molding possesses is of a higher value than that obtained from steady state measurements due in part to shrinkage of the material in a direction perpendicular to the contact plane (gapwise shrinkage). This shrinkage causes the surface of the a material, such as plastic, in an injection molding process, to move away from the mold surface. The magnitude of such movement at any point on the surface would depend upon the location of the contact point, the instantaneous time in the cooling cycle, and the injection molding parameters which control shrinkage. Computer simulation software can be used to predict this shrinkage profile at any given node, i.e., at a given distance from the interface of the plastic and the mold. Applicants discovered though that accurate experimental measurement of the corresponding thermal contact resistance values requires computation of thermal contact resistance as a function of time-dependent shrinkage, i.e., from a transient experiment.

Transient heat conduction requires the solution of the conduction equation. Since temperatures measured at a few locations (nodes) at discrete time intervals are available for the computation of thermal contact resistance, Applicants recognized that an inverse method of calculation has applications in a transient method of determining thermal contact resistance and thermal conductivity.

Furthermore, the present invention is based upon Applicants' recognition and selection of an appropriate conduction model for the processor experimental setup, and the development of a heretofore unknown procedure for simultaneously determining thermal conductivity and thermal contact resistance of a sample using an inverse method. Generally, an inverse method of solving a problem is to deduce a cause from an effect. For example, in a heat conduction problem, the known thermal properties are used to solve the heat conduction equation and to obtain the temperature distribution in a body. However, in an inverse problem, the temperature measurements at one or more locations are used to determine either the unknown properties or unknown boundary condition coefficients. If the property has a single value in a given experiment, the problem is called parameter estimation (for instance, determination of isotropic thermal conductivity which is independent of temperature); when the quantity to be determined is a function of time, temperature, or space, then the problem becomes one of evaluating a function, and is known as function estimation, and a cause (the parameters of the system) is sought given the effect (the output of the system for a given input).

With an apparatus or method of the invention, the quantity to be determined, such as thermal contact resistance or thermal conductivity, is defined as a discrete or continuous function and given an initial value which may be arbitrary or a guess value based on prior data, such as data obtained using steady state methods of determining thermal conductivity or thermal contact resistance. The heat conduction model is then solved and the temperature at a given location or node, at a given distance from the sample is obtained as the output. The temperature of blocks surrounding a sample is then measured at discrete time intervals at same location or node, for the same boundary conditions as those used in the solution of the heat conduction equation. An objective function, which is essentially the difference between the calculated and measured temperatures, is then used to determine a correction to the function to be estimated, which involves minimizing the object function with respect to the quantity to be estimated. The unknown quantity is then corrected iteratively until the minima is reached and convergence is obtained. As a result, properties such as thermal conductivity or thermal contact resistance of a sample determined with an apparatus or method of the invention are more accurate than those determined using a steady state method.

Apparatus of the Invention

A schematical drawing of an embodiment of an apparatus of the present invention is set forth in FIG. 1. Initially, a frame (1) is provided which has an upper plate (2), and a lower plate (3). Preferably, frame (1) is made of a material which can support its own weight, along with the weight of the apparatus, and can withstand changes in stress and temperature. An example of such a material is steel. In the embodiment of FIG. 1, a heat sink (4) is attached to lower plate (3) of frame (1). Numerous heat sinks have applications in an apparatus of the invention. In a preferred embodiment, heat sink (4) comprises a coiled metal tube or coiled tubular passage contained in a copper jacket (not shown), wherein the coiled metal tube or tubular passage contains a constant temperature bath of circulating heat transfer oil.

Again referring to FIG. 1, a first block (5) having an upper surface (6) and a lower surface (7) is mounted onto heat sink (4) such that lower surface (7) is in contact with heat sink (4). It is important that first block (5) be comprised of a material that has a melting point greater than the melting point of the sample, can conduct heat, and is able to withstand pressures greater than atmospheric pressure. Examples of such materials include, but are not limited to, copper, iron, steel, aluminum, gold, or a polymeric material, such as TEFLON. Preferably, first block (5) is comprised of mold steel.

Referring again to FIG. 1, a second block (8) having an upper surface (9) and a lower surface (10) is provided. Just as with first block (5), second block (8) conducts heat, has a melting point greater than the melting point of the sample, and is able to withstand changes in pressure. Examples of materials which can be used in second block (8) include a metal such as copper, iron, steel, aluminum, gold, or a polymeric material such as TEFLON, to name only a few materials. Preferably, second block (8) is comprised of mold steel. Upper surface (9) of block (8) is attached to plate (11) via a BAKELITE bracket (not shown). Located within the bracket and connected to upper surface (9) of block (8) is a heat source (12), wherein the heat source has a temperature greater than that of heat sink (4). As explained previously, numerous heat sources have applications in the present invention. Examples of such heat sources include a beam of electromagnetic radiation focused onto upper surface (9) of second block (8). Second Block (8) absorbs the energy of such a beam, and transduces the energy beam into heat. Other heat sources having applications herein are an electrical heater which undergoes joule heating, and combustion of an inflammable material, such as an alkane or an alcoholat the upper surface (9) of block (8). Preferably, heat source (12) comprises an electrical heater.

Again referring to FIG. 1, first block (5) and second block (8) are positioned in a manner such that upper surface (6) of first block (5) and lower surface (10) of second block (8) are parallel to each other, and define a sample chamber (13). A sample having a first and second surface can be placed in sample chamber (13), and in contact with first block (5) and second block (8). As a result, a first interface is formed between the first surface of a sample and lower surface (10) of second block (8), and a second interface is formed between the second surface of the sample and upper surface (6) of first block (5). The method of the present invention can simultaneously determine the thermal conductivity of the sample, as well as the thermal contact resistance of the sample at both interfaces. Furthermore, insulation (23) surrounds first and second blocks (5) and (8) respectively, so that heat generated by heat source (12) not lost to the surroundings, but rather is conducted through second block (8), the sample in sample chamber (13), and first bock (5) and is trapped in heat sink (4). Examples of insulation have applications in an apparatus of the invention include rubber, styrofoam, or fiberglass, to name only a few.

Referring once again to FIG. 1, a temperature sensing means (not shown) is connected to first block (5) and second block (8). As explained above, numerous temperature sensing means have applications in the present invention, such as a thermometer, a thermocouple, or an optical fiber fluorescent based temperature sensor, to name only a few. In a preferred embodiment, the temperature sensing means comprises a J-type thermocouple connected to first block (5) and second block (8) in at least two discrete locations, or nodes. Furthermore, first block (5) and second block (8) comprise at least two bores (14) running from a central axis of each block to the periphery of each block, and are perpendicular to the peripheries of blocks (5) and (8), so that bores (14) are parallel to the upper and lower surface of each block. The location, or nodes, of bores (14) are at specific distances from the respective interface of the sample in the sample chamber and the respective block. The temperature sensing means (not shown) is then inserted into the bores (14) of first block (5) and second block (8) such that the temperature sensing means makes contact with the respective blocks at their central axes. In a particular embodiment of an apparatus of the present invention, the temperature sensing means (not shown) is a J-type thermocouple inserted into the bores (14) of blocks (5) and (8) such that its tip makes contact with the respective block at its central axis. Optionally a thermal conductivity paste (not shown), which conducts an electrical current and heat, is also inserted into the bores (14) are used to ensure contact of the tip of the thermocouples (not shown) to blocks (5) and (8). Numerous such pastes are available and have applications in the present invention. A particular example of such a paste is "OMEGATHERM-201" produced by Omega Corporation, Stanford, Conn.

A temperature calculating means (not shown) is connected to the temperature sensing means connected to first block (5) and second block (8), which converts signals received from the temperature sensing means into a numerical temperature value. An example of such a calculating means comprises a computer (not shown) having a data acquisition system comprising an isothermal terminal block, multiplexer/signal conditioner and data acquisition board in computer.

Furthermore an apparatus of the present invention comprises a computing means for simultaneously determining the thermal conductivity of the sample, and the thermal contact resistance of the sample at the first and second interfaces. Such a means comprises a computer (nost shown) connected to the calculating means (or both could be part of the same computer), which then solves the following function using data taken on the temperature of first block (5) and second block (8) as a function of time:

$$\beta_{k+1}=\beta_k+[X^TWX+V]^{-1}[X^TW(T-\eta(\beta_k))+V(v-\beta_k)] \quad (1)$$

Figure 12A:
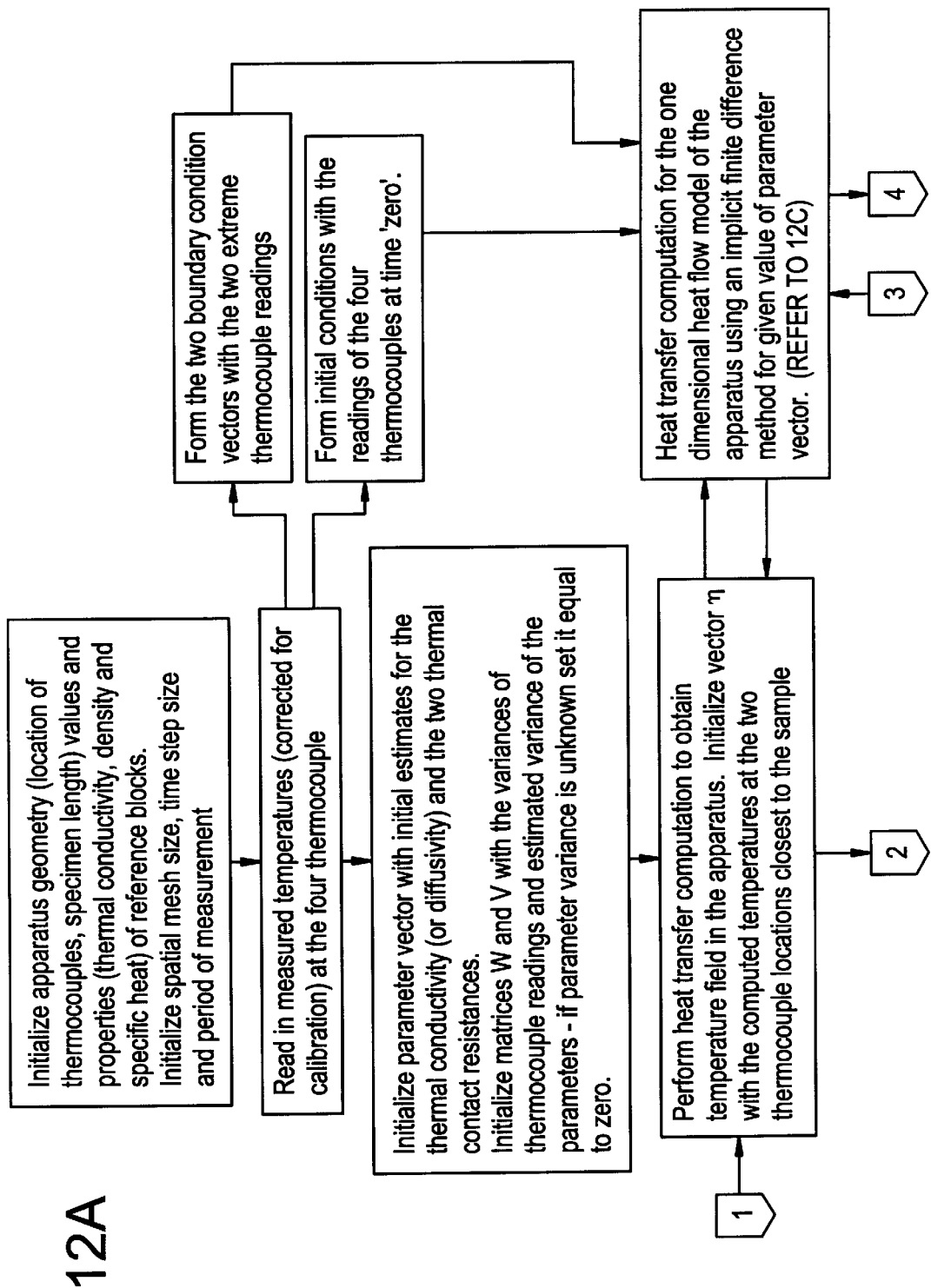
FIGS. 12A–12C are flow charts of the methodology for programming a computing means of an apparatus of the present invention to determine thermal conductivity and thermal contact resistance of a sample.
Figure 12B:
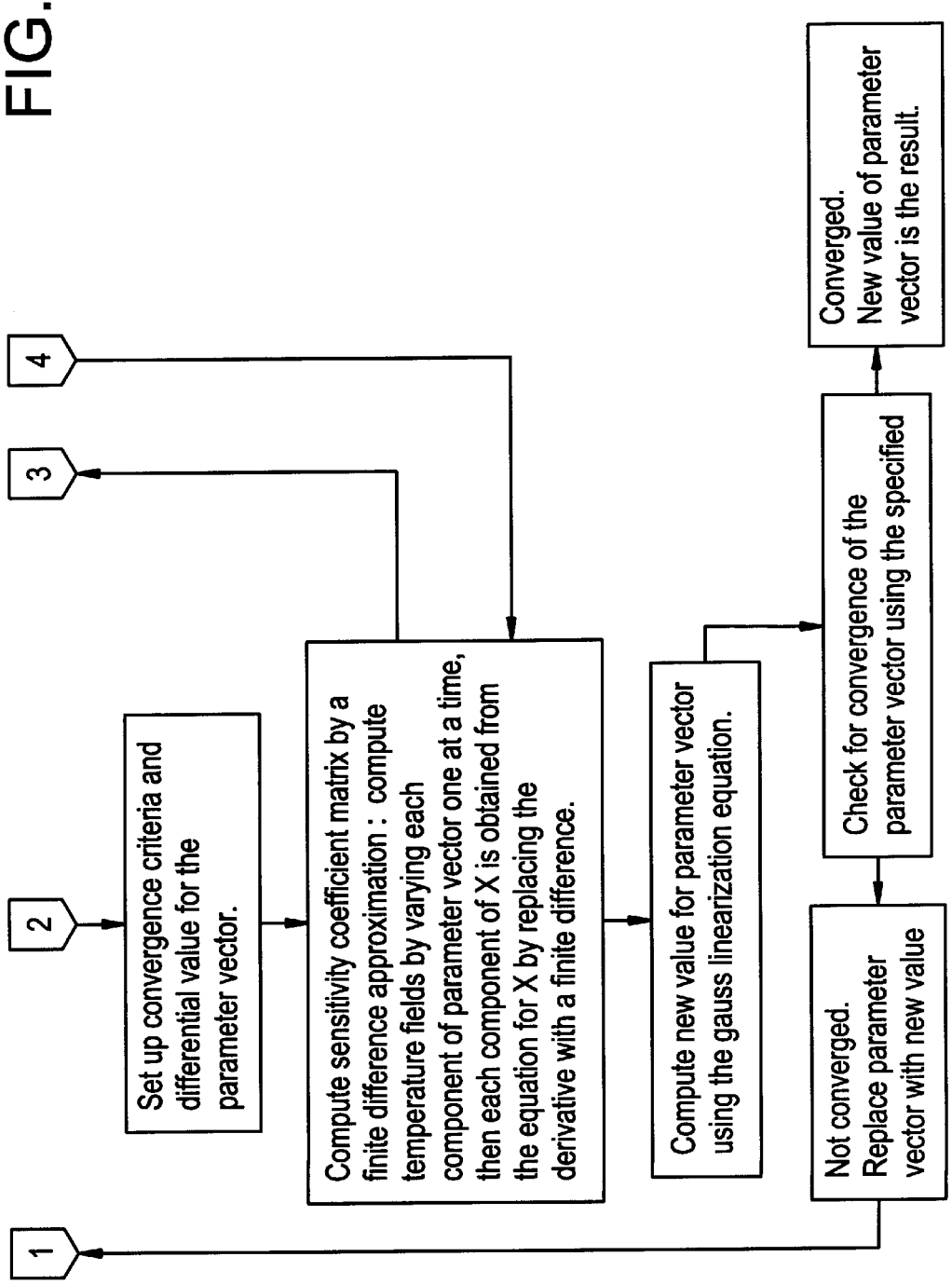

Pursuant to the present invention, the function can be solved using a methodology set forth in the Flow Chart of FIGS. 12a and 12b. Programming a computer to follow this methodology is readily apparent to one of ordinary skill in the art, and is not described here in detail.

Optionally, an apparatus of the present invention comprises a means of modulating the pressure or load on a sample in the sample chamber. An example of such a means includes a means of translating second block (8) towards first block (5) in such a manner that lower surface (10) of second block (8) remains parallel to upper surface (6) of first block (5). Referring to FIG. 1, at least two guide rods (15) are connected to lower plate (3) of frame (1) such that they are perpendicular to plate (3). Preferably the at least two guide rods (15) are positioned such that heat sink (4), first block (5) and second block (8) are located between them. Furthermore plate (11) comprises at least two holes (22) through which at least two guide rods (15) pass through plate (11), with one guide rod (15) passing through one hole (22). Moreover, an externally threaded rotatable shaft (16) having an upper end (17) and a lower end (18) is provided. Shaft (16) engages an internally threaded bore (19) in upper plate (2) of frame (1). Lower end (18) of shaft (16) is in contact with plate (11). When shaft (16) is rotated, lower end (18) exerts a pressure on plate (11). As a result, guide rods (15) penetrate plate (11), and second block (8) is translated towards first block (5) in a manner such that lower surface (10) of second block (8) remains parallel with upper surface (6) of first block (5), and the pressure or load upon a sample in sample chamber (13) is increased. Rotation of shaft (16) can be accomplished manually or automatically, in that it can be connected to an automatic rotating means. In a particular embodiment of the invention, rotation of shaft (16) is accomplished manually. In particular, a handle (20) affixed to upper end (17) of shaft (16) can be used to rotate shaft (16) so that shaft (16) translates first block (5). As a result, when plate (11) is translated while guide rods (15) pass therethrough via holes (22) in plate (11), second block (8) is translated towards first block (5) in a manner such that lower surface (10) of second block (8) remains parallel with upper surface (6) of first block (5). Consequently, the volume of sample chamber (13) is decreased, and pressure or load upon a sample in sample chamber (13) increases. Optionally a load cell (21) located between lower end (18) of shaft (16) and plate (11) can be used to determine the load upon a sample in sample chamber (13).

An example of a method of the present invention using an apparatus schematically shown in FIG. 1 and described above initially involves placing a sample in sample chamber (13). Optionally, the pressure upon the sample may be increased using a pressure modulating means, an example of which is described above, and the thermal conductivity and thermal contact resistance of two interfaces of the sample can be determined relative to the pressure or load on the sample.

After the sample is placed in chamber (13), and optionally its pressure is increased, its temperature is modulated. This temperature modulation may involve heating the sample via heat conduction from heat source (12) until the sample reaches a constant temperature, turning off the heat source (12) and then determining the temperatures of the first and second blocks (5 and 8) as a function of time. An alternative method involves starting at a specific temperature, such as room temperature, and increasing the temperature of the sample by generating heat with heat source (12) while measuring the temperature of first blocks (5) and second block (8) at specific locations or nodes relative to the interface of the respective block with the sample in sample chamber (13) as a function of time. These temperature measurements are then used to determine simultaneously thermal conductivity of the sample, and thermal contact resistance at the first and second interfaces of the sample with blocks (5) and (8) using equation 1, and methodology discovered by Applicants and set forth in the flow chart of FIGS. 12a and 12b.

Inverse Formulation Having Applications in an Apparatus and Method of the Invention The inverse problem formulation starts initially with an object function $S(\beta)$, which is defined as:

$$S(\beta)=[T-\eta(\beta)]^T w[T-\eta(\beta)]+(v-\beta)^T V(v-\beta) \quad (2)$$

where $\eta(\beta)$ is the vector of temperature values at a particular location (node) in the apparatus as obtained from a physical model of the apparatus; T is the vector of temperatures measured at that location over a given interval of time; and V is a measure of the variance of $\beta$. The vector $\beta$ consists of parameters to be estimated and has the form $[k, R_{c1}, R_{c2}]$, where $k, R_{c1}, R_{c2}$ are again vectors whose components are the values of the parameters at each instant of time over which the temperatures are measured, e.g., the thermal conductivity of the sample, the thermal contact resistance at the first interface between the sample and another material, and the thermal contact resistance at the second interface of the sample with another material.

The objective function is then minimized by iteratively generating new values of the parameter vector starting with an initial guess. An appropriate guess would be well within the knowledge of one of ordinary skill in the art. The Gauss method of linearization has been used here to generate the new iterates, as simulation shows that it provides reasonably quick convergence. Another factor recognized in selecting the inverse method was the knowledge of the approximate range of the parameter values. A new set of parameter values are then obtained from $$\beta_{k+1}=\beta_k+[X^T WX+V]^{-1}[X^T W(T-\eta(\beta_k))+V(v-\beta_k)] \quad (1)$$

where X is the sensitivity matrix, and is a measure of the variation in the temperature distribution for a small variation of the components of $\beta$. Essentially, an apparatus of the present invention provides a one dimensional heat flux across the sample in the sample chamber, such that the sample is sandwiched between the first and second blocks. Thus, the one dimensional heat conduction equation $$(\partial/\partial x)(k)(\partial T/\partial x)=C(\partial T/\partial t) \quad (3)$$

can be used to model an apparatus of the invention and generate the vector $\eta(\beta)$ for each new set of values in $\beta$. In equation (3), C is the heat capacity of the sample. The heat equation can be solved by an implicit finite difference algorithm with a prescribed condition. A finite difference method can also be employed to compute X.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE

Thermal conductivity of polymers and thermal contact resistance at the interface between plastics and other materials are important parameters in the simulation of plastic processing techniques. As a follow-up to the experimental results obtained under steady state conditions, an inverse method was developed for the computation of thermal contact resistance and thermal conductivity, using transient temperature measurements. The method involves temperature measurement on a one dimensional heat flow apparatus under transient heat flow conditions and has been tested using simulated data. The inverse procedure used minimizes a suitably defined sum of squares function to obtain the heat transfer parameters. The method, though computationally more intensive compared to steady state methods, requires no a priori knowledge of the thermal conductivity or the thermal contact resistance, and no location of thermocouples in the sample. Furthermore, it reduces the experimental time considerably compared to the steady state method set forth herein.

Nomenclature

C is heat capacity $(j/m^3-K)$, k is thermal conductivity (W/m-K), $R_c$ is thermal contact resistance $(m^2-K/W)$, n,m are number of points at which k and $R_c$ are defined, respectively, t is time (seconds), T is Temperature, vector of measured temperature (C.), V is variance matrix, W is weighting matrix, x is axial distance (m), X is sensitivity matrix=$[\partial \eta_i/\partial \beta_j]$, $\beta$ is parameter vector=$[k_{t=1,n}\ R_{c1}|_{t=1,n}\ R_{c2}|_{t=1,n}]^T$, $\eta$ is Temperature, vector of temperatures from physical model of apparatus (°C.), v is initial value of $\beta$, $R_S$ is the thermal resistance of the sample=$t/kA(m^2-K/W)$, $t_h$ is sample thickness (m), A is surface area $(m^2)$, subscripts 1,2 are upper and lower interfaces between plastic specimen and steel blocks, respectively.

Introduction

Thermal conductivity of a given material is a function of temperature and pressure and hence its measurement at steady state conditions can be used to define it as a function of these two thermodynamic properties. Transient methods of measuring thermal conductivity mainly serve to reduce the time required to perform the experiment as attaining steady state in terms of temperature reading is a time consuming process. Thermal contact resistance (TCR), on the other hand, is both a surface and volume phenomenon. If the interface is subjected to a steady state condition, or if the value of TCR is of significance only when steady state operating conditions are attained, then TCR depends on the interface contact pressure, nature of the surfaces in contact, thermal conductivity of the contacting materials and interstitial media (Fletcher, 1988). Under such conditions, TCR has been shown to be generally independent of temperature (Peterson and Fletcher, 1988; Rhee et al. 1993). However in certain applications, such as in processing of materials, the contact resistance is no longer independent of the temperature as one of the surfaces in contact is in the process of formation (Yu et al. 1990). As a result, the interfacial gap, which eventually determines the TCR value, is a function of both time and space. It is thus no longer sufficient to study TCR based on steady state conditions alone, either analytically or experimentally.

The time dependent TCR to be studied now appears as a boundary condition in a problem modeled by the heat conduction partial differential equation. Inverse methods are powerful techniques for estimating such unknown functions appearing as boundary conditions for the solution of differential equations. However, inverse problems are generally ill-posed (Dulikravich and Martin, 1997), sensitive to measurement errors and require very careful design of the experimental and solution technique along with an understanding of the process to provide the correct solution.

Experimental Measurement of Thermal Contact Resistance Under Steady State Conditions Thermal contact resistances at plastic-metal interfaces have been investigated recently for the purpose of incorporating the effect into software codes for the simulation of plastic processing techniques—the most important one being injection molding. Yu et al. (1990) determined a value of the thermal contact resistance for injection molding using temperature measurements in the mold during actual injection molding. They calculated the TCR by computing the temperature on either side of the interface from measured temperatures using the one-dimensional heat conduction equation. The results were presented in the form of material and part thickness dependent TCR. They used values of the order of $10^{-3}$ $m^2$-K/W (the actual values were material and thickness dependent) in their simulations and found that the use of these values in the simulation of cooling times improved the simulation results very significantly when compared with cooling times measured during actual molding of the part. Rhee et al. (1993) and, Narh and Sridhar (1997) measured the TCR of polystyrene sample using a steady state method and a one-dimensional heat flow meter type apparatus, and found that the TCR at an interface between typical mold type metal surface and a polystyrene sample at temperatures below the glass transition temperature ($T_g$) of polystyrene was of the order of $5$–$8 \times 10^{-5}$ $m^2$-K/W. The experimental procedure, apparatus and the main results are summarized in the following sections.

Determination of Thermal Conductivity and Average Thermal Contact Resistance Using a Steady State Method For a material obeying Fourier conduction, the thermal resistance it offers to one dimensional heat transfer is a linear function of its thickness (everything else remaining constant). The total resistance $R_t$ of such a sample with identical surface characteristics on both sides, when sandwiched between two contact surfaces is given by the equation:

$$R_t = R_s + 2R_c \quad (4)$$

where $R_s = t_h/kA$ is the thermal resistance of the sample $t_n$, the specimen thickness, k thermal conductivity and A the cross sectional area. This relation can be used to determine both the thermal conductivity and the contact resistance by a regression procedure depending on the number of independent parameters that are varied during the measurement. In our case, we measured the total resistance of a number of specimens of different thicknesses and same area at a constant pressure and temperature. Using Eq. (4), the total resistance can be expressed as:

$$R_t = \Delta T/q \quad (5)$$

where $\Delta T$ now denotes the temperature drop between the two contact surfaces between which the specimen is sandwiched. Then for the case of one dimensional steady state heat flow the total resistance becomes a simple linear function of thickness:

$$R_t = (1/kA)t_h + 2R_c \quad (6)$$

The slope of the line fit through the points ($R_t$, $t_h$) yields the thermal conductivity and the intercept is equal to $2R_c$. The thermal conductivity of the sample is assumed to be constant in the range of temperatures across the sample, or the thermal conductivity determined can be considered as the effective thermal conductivity at the mean temperature of the sample.

Apparatus Used in a Steady State Method

Figure 12C:
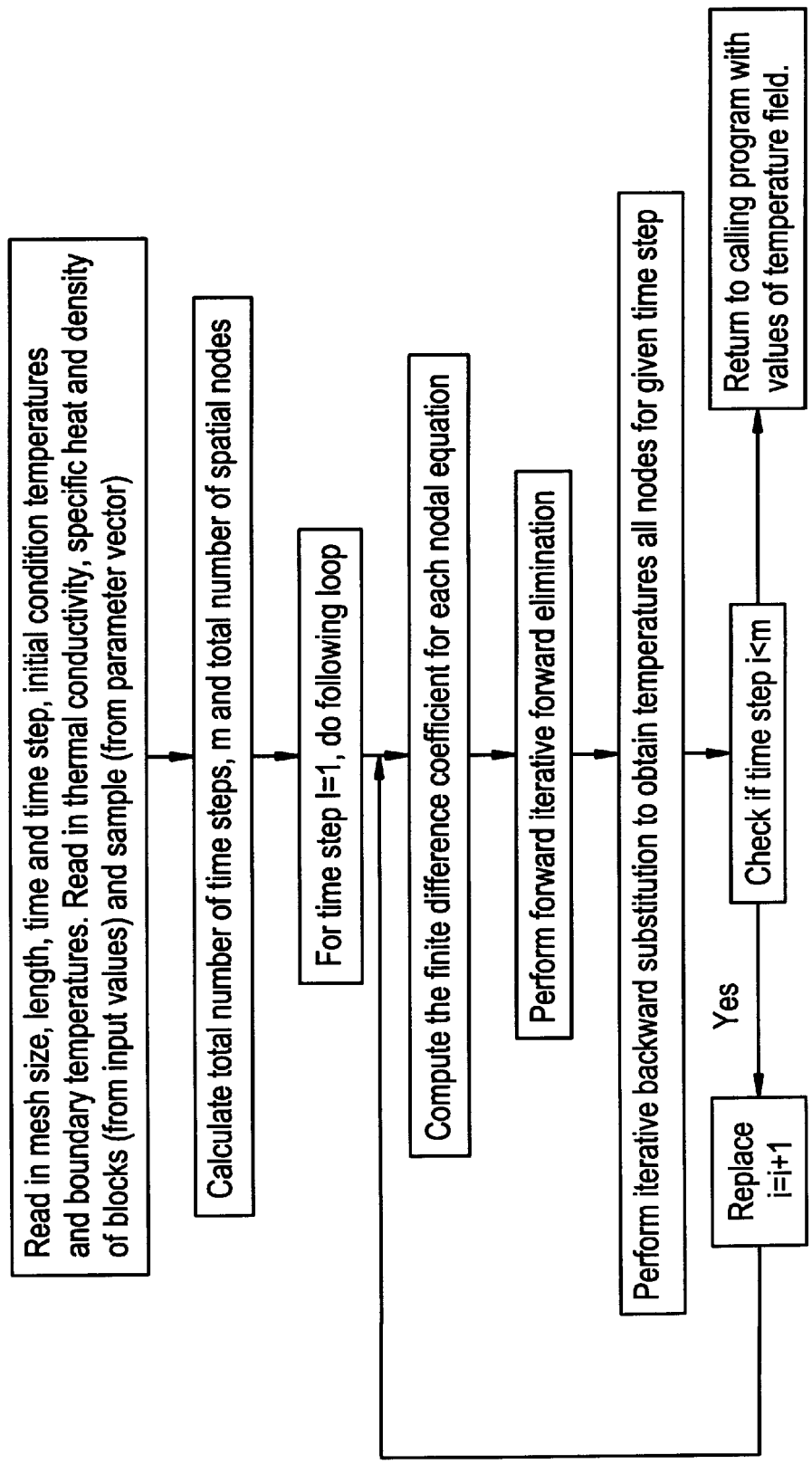

Generally, an apparatus for determining thermal conductivity and average thermal contact resistance of two interfaces of a sample is similar to an apparatus of the invention as set forth FIG. 1. However, a critical difference is that an apparatus of the present invention comprises inter alia, a computing means for determining simultaneously thermal conductivity and thermal contact resistance of two interfaces of the sample, wherein the computing means is programmed to solve Eq. (1) using a methodology set forth in the flow chart of FIG. 12. In contrast, an apparatus used in a steady state method determines thermal conductivity and average thermal contact resistance of two interfaces using equations (4)–(6). More specifically, an apparatus which utilizes the steady state method has an upper cylindrical block made of mold steel attached to a thick rigid steel plate using a BAKELITE bracket. A lower steel block, also fabricated from the same mold steel, is provided, and mounted on a copper jacketed heat sink which is attached to the lower steel plate of the frame. A constant temperature bath maintains the temperature of the sink at a set value of a circulating heat transfer oil.

The BAKELITE bracket described above houses an electrical heater, and a load cell is attached to the top of the plate to record the applied load. The plate is supported on a steel frame which permits it to move up and down while maintaining the parallelism between the bottom surface of the top steel block and the top surface of the lower steel block. The steel blocks have holes drilled perpendicular to their central axes to permit J type thermocouples to be inserted into the blocks and are in contract with the central axes of the blocks. A thermal conductivity paste is used to ensue good contact between the thermocouple tip and the mold steel of the blocks. The entire apparatus is then placed in a rigid steel frame which permits modulation of pressure on the top of the load cell, and application of a constant pressure to the load cell. Once the electrical heater is turned on, and generating heat such that a steady state has been attained, the thermocouple readings are recorded through a data acquisition system consisting of an isothermal terminal block, multiplexer/signal conditioner and a data acquisition board in the computer.

Sample Preparation With a Steady State Method

Polystyrene was used in this preliminary study as its thermal and physical properties have been extensively studied and thus can be used as a reference to establish the accuracy of our data. 38.2 mm diameter polystyrene disk samples were compression molded. A brass shim was used to obtain uniformity of thickness to within 25 $\mu$m. The thickness of the sample was measured by taking readings along the periphery as well as at the center. In the present study the effect of varying the surface roughness has not been considered. Hence, to bring all samples to the same state at the contact plane in the apparatus, each sample was initially conditioned by heating it to approximately 100° C. between the steel blocks on the apparatus, and maintained at that temperature for approximately 25 minutes. The steel blocks and the sample were then brought to a constant temperature less than 100° C., at which temperature measurements were to be made.

Measurement Procedure With the Steady State Method

The sample was placed into a sample chamber defined by the two mold faces, and insulation was placed around it. Once the surfaces of the sample had been conditioned, as described above, the temperature of the sink was adjusted and the heater input controlled using a rheostat, to obtain a temperature gradient of about 10° C. between the heater and the sink. The TCR measurements were conducted at average specimen temperatures of 75° and 65° C. The heater and bath settings were first adjusted to obtain the required mean sample temperature and the required temperature gradient. For each heater and bath setting the load on the specimen was increased stepwise and thermocouple and load cell readings were taken when steady state was reached. Steady state was generally reached after 1 hour from the instant the heater setting was changed. For subsequent load changes steady state was reached in about 20 minutes.

Figure 2:
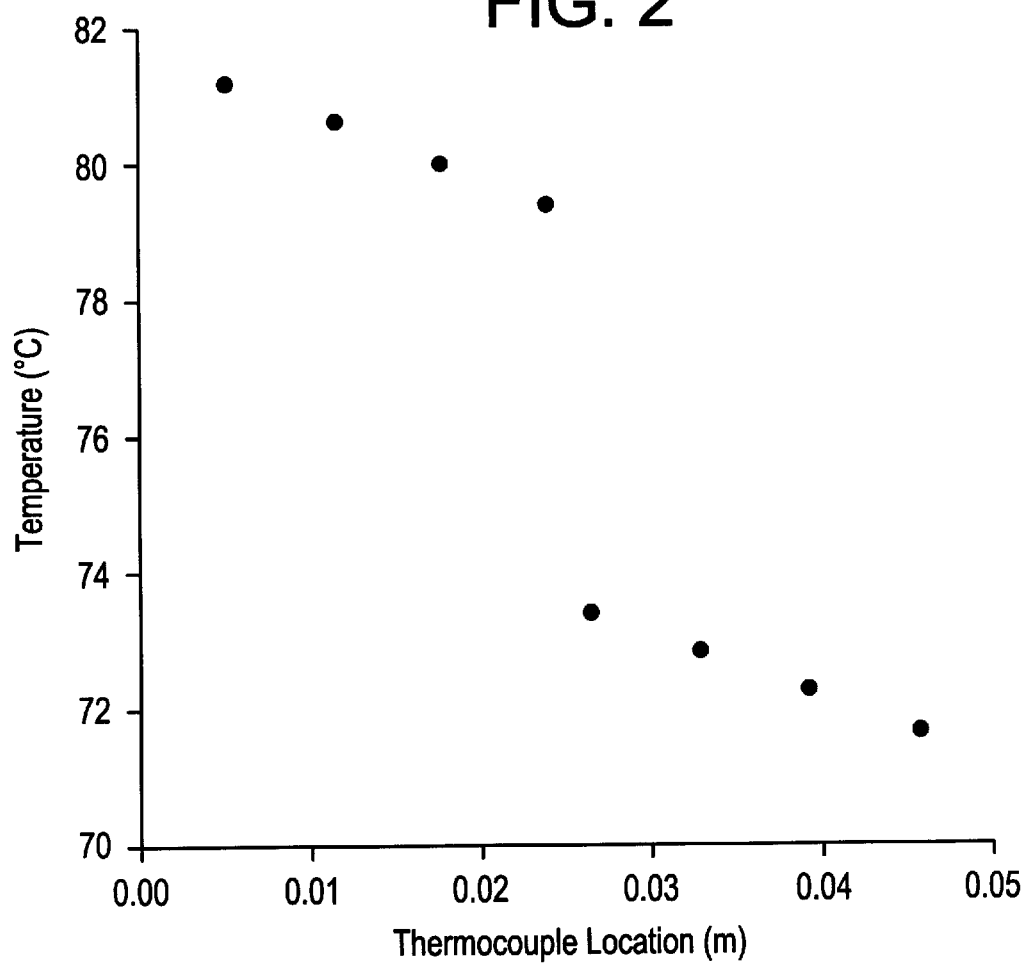
FIG. 2 is a graph of typical thermocouple readings along blocks' of an apparatus of the present invention. In the first block, the readings run from the upper surface to the lower surface, i.e., away from the sample chamber. In the second block, the readings are taken from the upper surface to the lower surface, i.e., towards the sample chamber.
Figure 3:
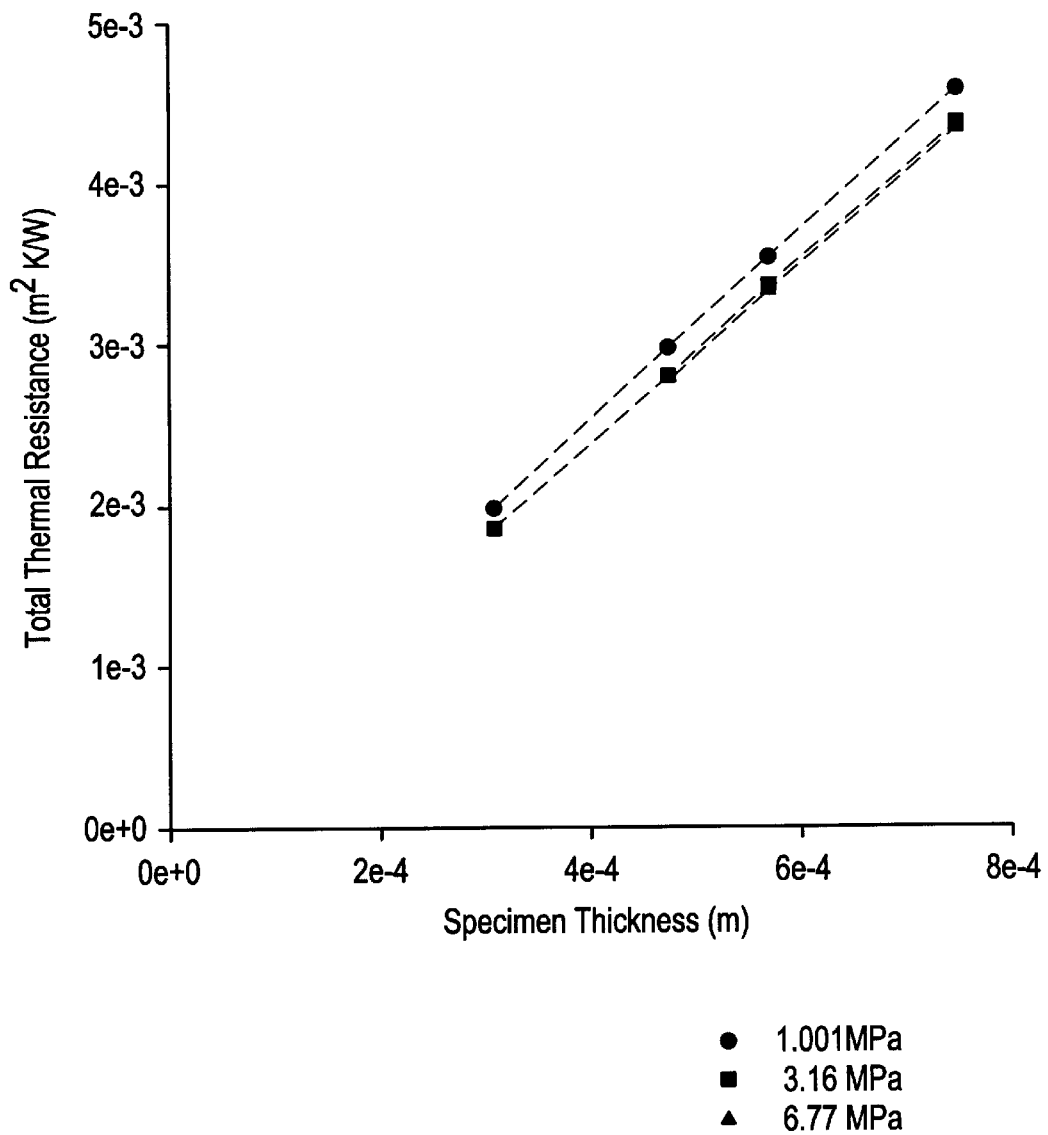
FIG. 3 is a graph of total thermal resistances of polystyrene samples versus sample thickness for different pressures.

The thermocouple readings were plotted against the axial distance as shown in FIG. 2 and the gradient of the best fit line multiplied by the known conductivity of the steel block gives the computed heat flux. The intercept of these two lines (temperature gradients in the two steel blocks) with the block surfaces in contact with the plastic specimen gives the temperature of the surfaces in contact with the specimen. The total thermal resistance of the specimen is then computed using Eq. (6). $R_t$ is plotted against specimen thickness as shown in FIG. 3. The TCR and thermal conductivity are then calculated as the intercept and slope respectively of the best fit straight line.

Measurements for different loads were carried out at two different mean temperatures. The sample thicknesses were measured at the end of the experiment when the apparatus had reached room temperature. No corrections were made to the values of thickness of the sample to account for the strain effects under load as the computed strain in these range of loads was less than the variation in sample thickness. However, the sample thickness was measured before and after the experiment to check that undue deformation did not occur.

Sample Experimental Results Using the Steady State Method

Figure 4:
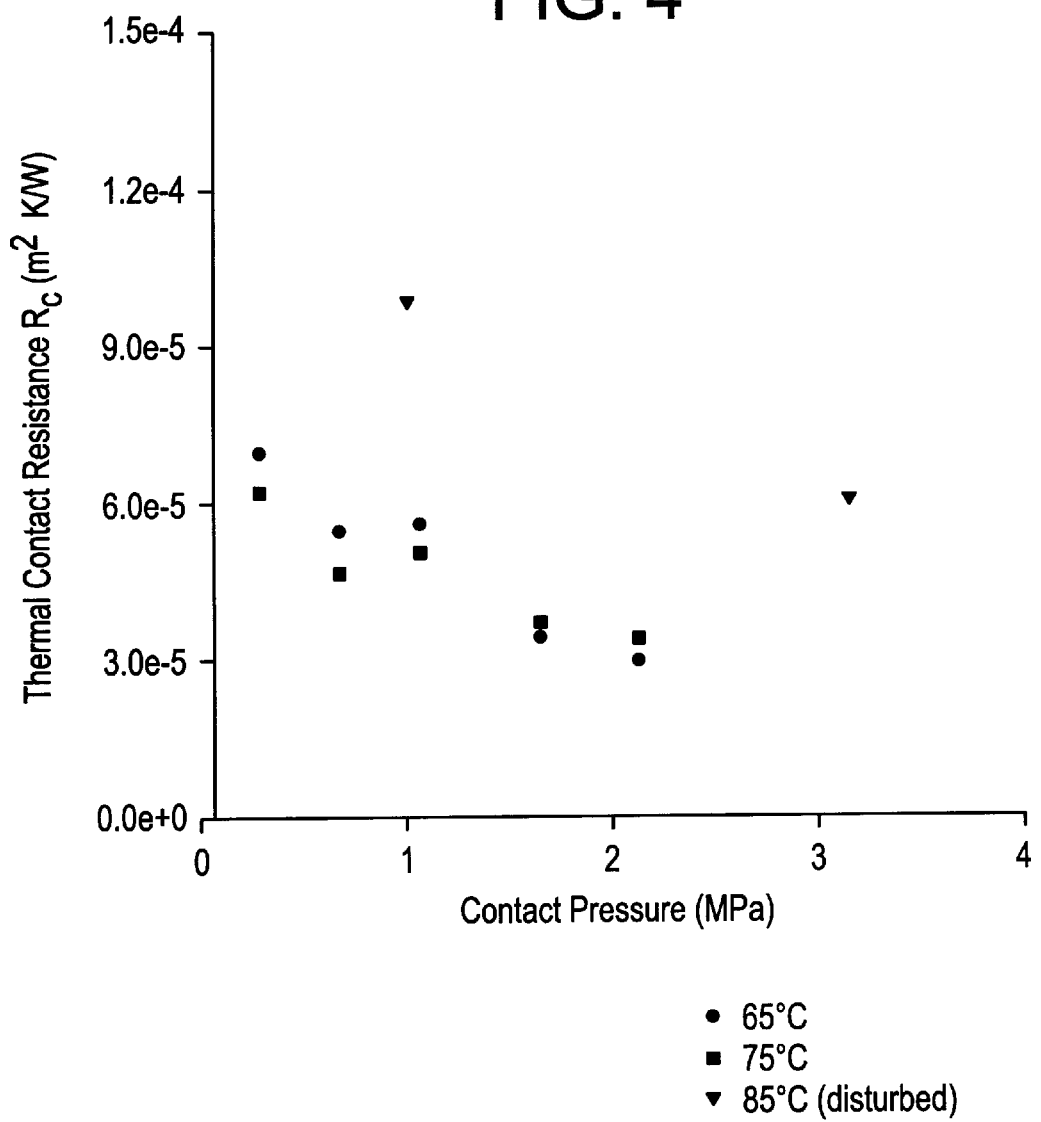
FIG. 4 is a graph of average thermal contact resistance versus contact pressure on a sample for different conditions using a steady state method for determining thermal contact resistance.
Figure 5:
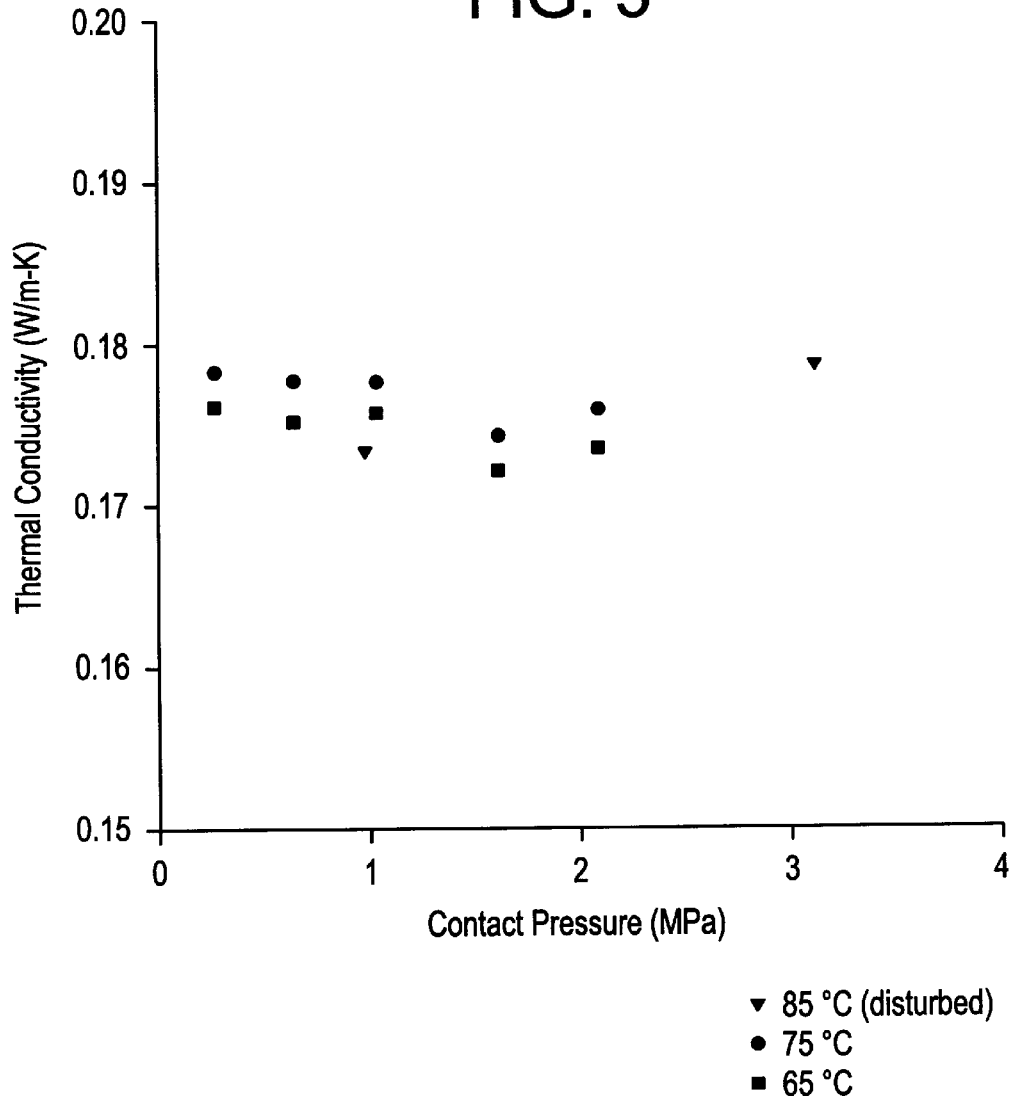
FIG. 5 is a graph of thermal conductivity of a sample verses contact pressures of sample for conditions the same as those used in FIG. 4, wherein the thermal conductivity is determined using a steady state method.

FIG. 4 shows sample plots for TCR as function of contact pressure for a series of temperatures. FIG. 5 shows the corresponding thermal conductivity as a function of contact pressure. As seen in FIG. 4 the TCR dropped initially and then tended to a limiting value, as the pressure was increased. These values are lower than those reported by Yu et al. (1990). Although under no obligation to do so, and not intending to be bound thereby, to explain the difference between their values and those of Yu et al., Applicants initially postulated that the thermal contact resistance increased at the interface due the shrinkage of the plastic in the direction parallel to the interface plane. Such shrinkage would cause the very good contact formed between the metal and plastic surface during the filling stages of injection molding when the soft plastic was pressed against the mold surface, to break. To test this hypothesis, TCR of a sample was measured after the interface was formed during the conditioning process described in the preceding sections. Then the measurements were repeated after the interface was disturbed by a slight rotation of the sample about its vertical axis. The results of the second measurements (to be referred as disturbed interface results), are also plotted in FIGS. 4 and 5. From FIG. 4, it is apparent that the movement of the interface has resulted in increased TCR, but to values that are still below those of Yu et al.

In a recent paper Mohr et al. (1997) concluded that TCR at an elastomer-elastomer interface depends on the flatness rather than on microscopic asperities. At lower contact pressures, deviation from the surface flatness causes much larger interfacial gaps and, hence, larger TCR values than those due to microscopic asperities. Consequently, although under no obligation to explain such results, and not intended to be bound by such an explanation, Applicants have hypothesized that the TCR in injection molding processes could be of higher value than that obtained from steady state measurements due to part shrinkage in the direction perpendicular to the contact plane (gapwise shrinkage). This shrinkage would cause the plastic surface to move away from the mold surface. The magnitude of such movement at any point on the surface of the plastic would depend on the location of the contact point, the instantaneous time in the cooling cycle, and the injection molding parameters which control shrinkage. Computer simulation software can be used to predict this shrinkage profile at any given node. However, the experimental measurement of the corresponding TCR requires computation of TCR as a function of time-dependent shrinkage—i.e. from a transient experiment.

Transient heat conduction requires the solution of the conduction equation. Since temperatures measured at a few locations at discrete time intervals are available for the computation of TCR, inverse methods are well suited for this purpose. The sections which follow describe an inverse method which Applicants have developed to study the transient TCR.

The Inverse Method Employed in the Present Invention

The inverse problem formulation follows the method outlined in Beck and Arnold (1974) and Jurkowski et al. (1989). An objective function $S(\beta)$ is defined as $$S(\beta)=[T-\eta(\beta)]^T W[T-\eta(\beta)]+(v-\beta)^T V(v-) \quad (2)$$

where $\eta(\beta)$ is the vector of temperature values at a particular location in the apparatus as obtained from a physical model of the apparatus, T is the vector of temperatures measured at that location over a given interval of time and V is a measure of the variance of $\beta$. The vector $\beta$ consists of parameters to be estimated and has the form $[k, R_{c1}, R_{c2}]$, where k, $R_{c1}$ and $R_{c2}$ are again vectors whose components are the values of the parameters at each instant of time over which the temperatures are measured.

The objective function is minimized by iteratively generating new values of the parameter vector starting with an initial guess. The Gauss method of linearization has been used here to generate the new iterates, as simulation shows that it provides reasonably quick convergence. Another factor that lead to the selection of this method was the knowledge of the approximate range of the parameter values. The new set of parameter values are then obtained from $$\beta_{k+1}=\beta_k+[X^TWX+V]^{-1}[X^TW(T-\eta(\beta_k))+V(v-\beta_k)] \quad (1)$$

where X is the sensitivity matrix, and is a measure of the variation in the temperature distribution for a small variation of the components of $\beta$. The apparatus used essentially provides a one dimensional heat flux across a plastic specimen sandwiched between two steel blocks. Thus the one dimensional heat conduction equation $$(\partial/\partial x)(k)(\partial T/\partial x)=C(\partial T/\partial t) \quad (3)$$

was used to model the apparatus and generate the vector $\eta(\beta)$ for each new set of values of $\beta$. In Eq. (3), C is the heat capacity. The heat equation was solved by an implicit finite difference algorithm with a prescribed temperature boundary condition. A finite difference method was also employed to compute X.

Figure 6:
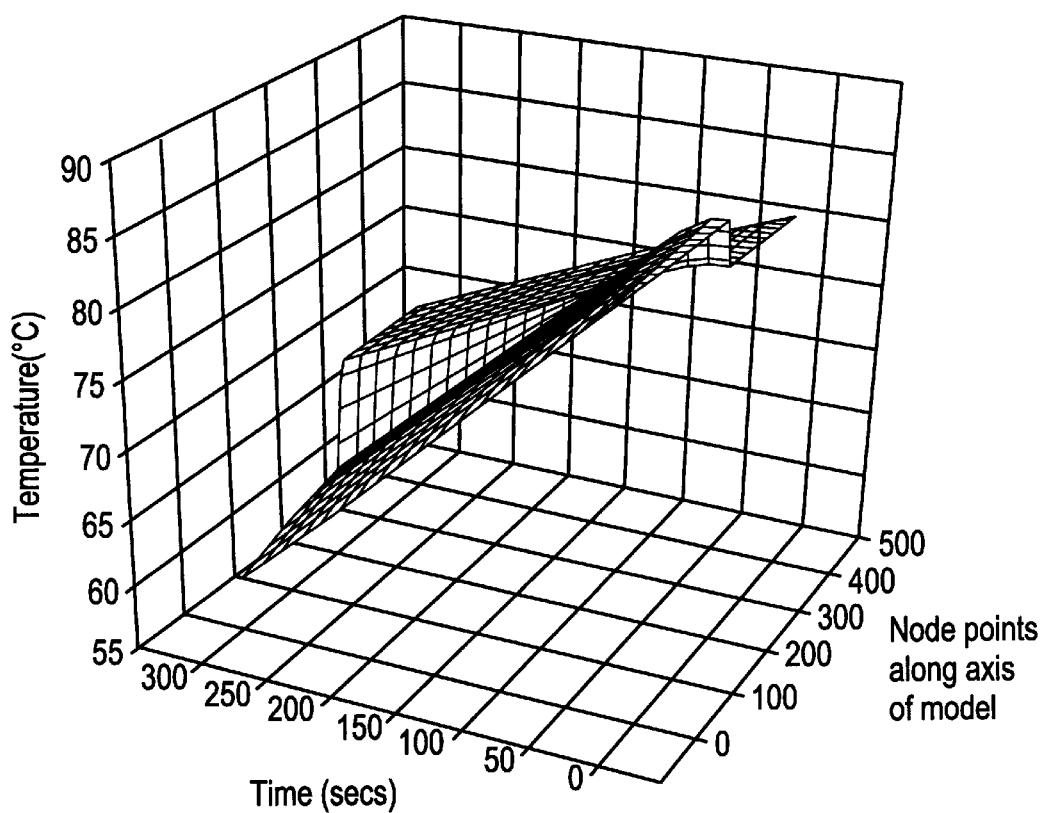
FIG. 6 is a graph of the results of simulation as a mesh of the transient temperature distribution in a model.
Figure 7:
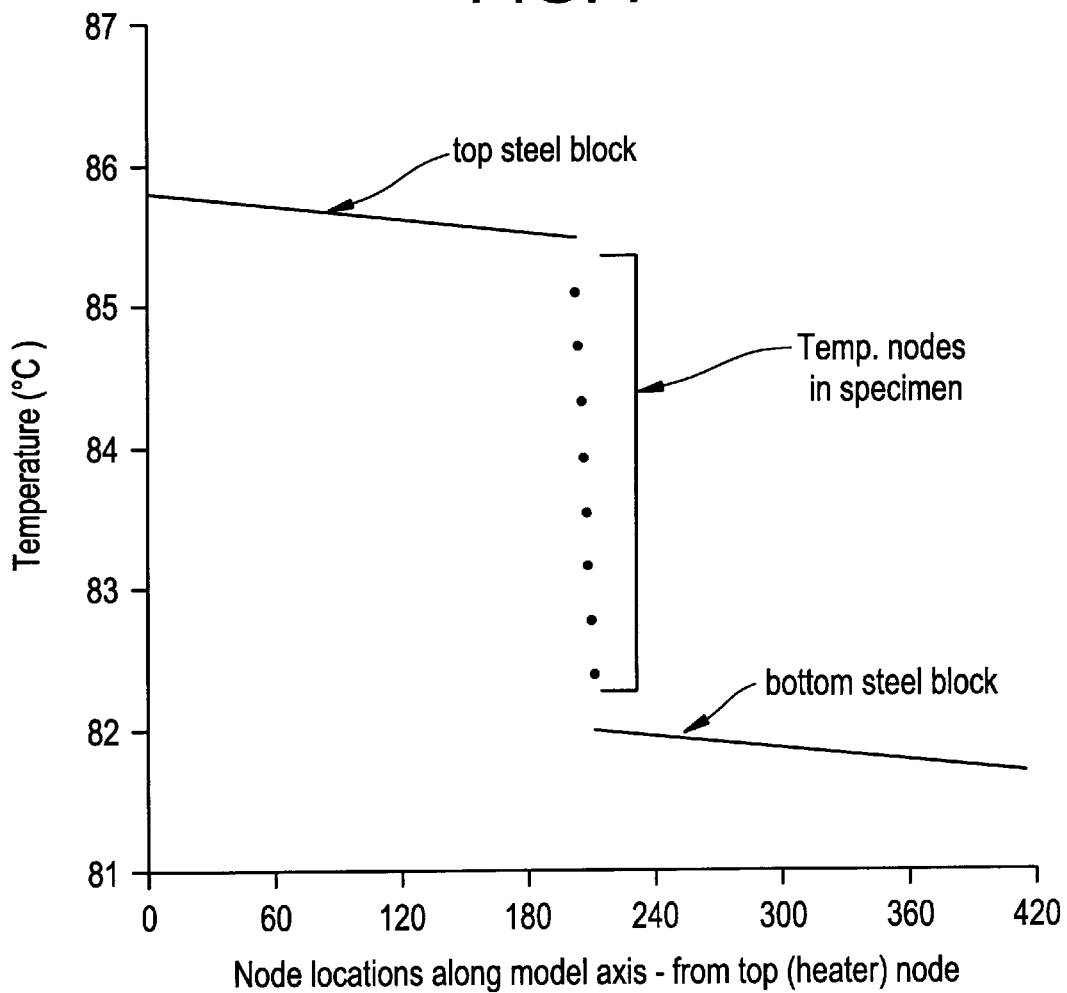
FIG. 7 is a graph of the temperature distribution at t=0 seconds, used as an initial condition for simultaneously determining thermal conductivity and thermal contact resistance at two distinct surfaces of a sample using a method and apparatus of the present invention.
Figure 8:
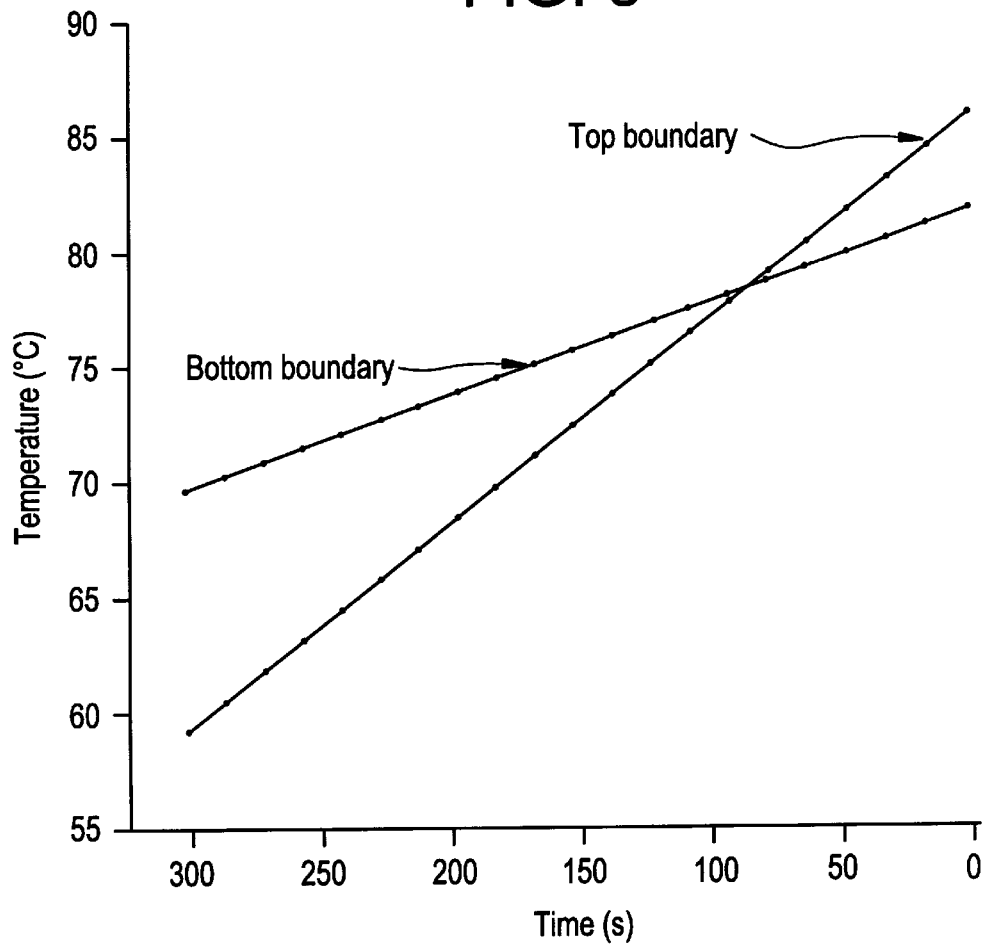
FIG. 8 is a graph of the temperature distribution at two extreme nodes for time t=0 and t=300 seconds, used as boundary conditions of the sample for calculation of thermal conductivity with the present invention using an inverse algorithm. The two nodes correspond to the heat source and the heat sink on the apparatus of the present invention. Note, the scale on abscissa has been re-oriented to match the mesh in FIG. 6.

Experimental Procedure Using the Apparatus and Method of the Present Invention Simulation Simulations were performed using a model of an apparatus schematically shown in FIG. 1, comprising, inter alia, a computing means, such as a computer programmed to solve Eq. (1) using a methodology set forth in the flow chart of FIGS. 12a and 12b. The simulations were performed by generating the temperature distribution in the apparatus with an assumed value of the parameter vector $\beta$, in this case [0.17, 0.0001, 0.00018]. The value of the thermal conductivity corresponds to a typical value for polystyrene, a widely studied plastic (see also FIG. 5). The contact resistance values are in the range of the measured values from steady state experiments shown in FIG. 4 and reported previously (Narh and Sridhar, 1997). The thermal conductivity and the contact resistances were assumed constant with time. The assumption is based on the temperature range used in the stimulation—in this range the variation in thermal conductivity is of a small order, and for a plastic well below its glass transition temperature (100° C. for polystyrene), the TCR can be assumed to be constant with time. The rationale behind this assumption is that for temperature below $T_g$, the surface of the plastic has an approximately constant value of hardness. The stimulation was started with an initial temperature distribution as shown in FIG. 7 and boundary conditions shown in FIG. 8. FIG. 6 maps the simulated temperature distribution which was used for the inverse solution and from which FIGS. 7 and 8 are derived.

Solution

The stimulated temperatures were used to initialize three vectors containing the initial conditions, boundary conditions and the measurement vectors. The initial conditions for the finite difference algorithm for Eq. (6) were obtained from the temperatures of all spatial nodes at time t=0, shown in FIG. 7. The prescribed temperature boundary conditions were formed from the temperatures at the two outermost nodes from time t=0 to time t=300 s. The measured temperature vector was formed with the readings of the node at a distance of 0.0012 m from the upper interface of the steel block. This corresponds to the location of the thermocouple closest to the upper steel-plastic interface in the experimental apparatus. Noise in the form of normally distributed random numbers, generated with zero mean and variance equal to typical variance of the thermocouple measurements was added to the 'measured' temperature vector T. The parameter vector was initialized with a guess set of values for the optimization to commence. Each iteration of the optimization loop involved the calculation of the sensitivity matrix X by a first order finite difference method. A new set of parameter vector values were calculated at each iteration and used in the finite difference algorithm for Eq. (6). The iteration was continued until the maximum change in any element of the parameter vector in successive iterations was less than 1%.

Results and Disscussion

Figure 9:
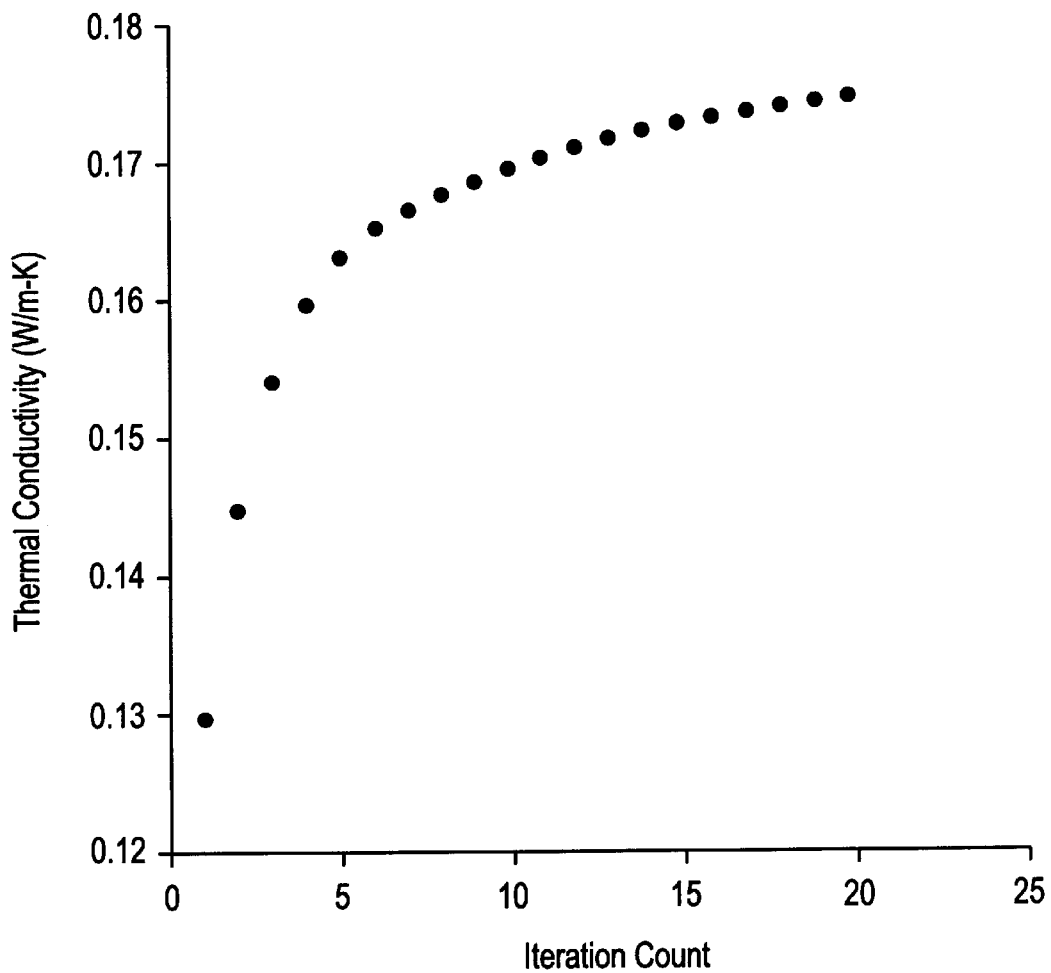
FIG. 9 is a graph of the determination of the thermal conductivity from simulated transient data (with noise) using the present invention.
Figure 10:
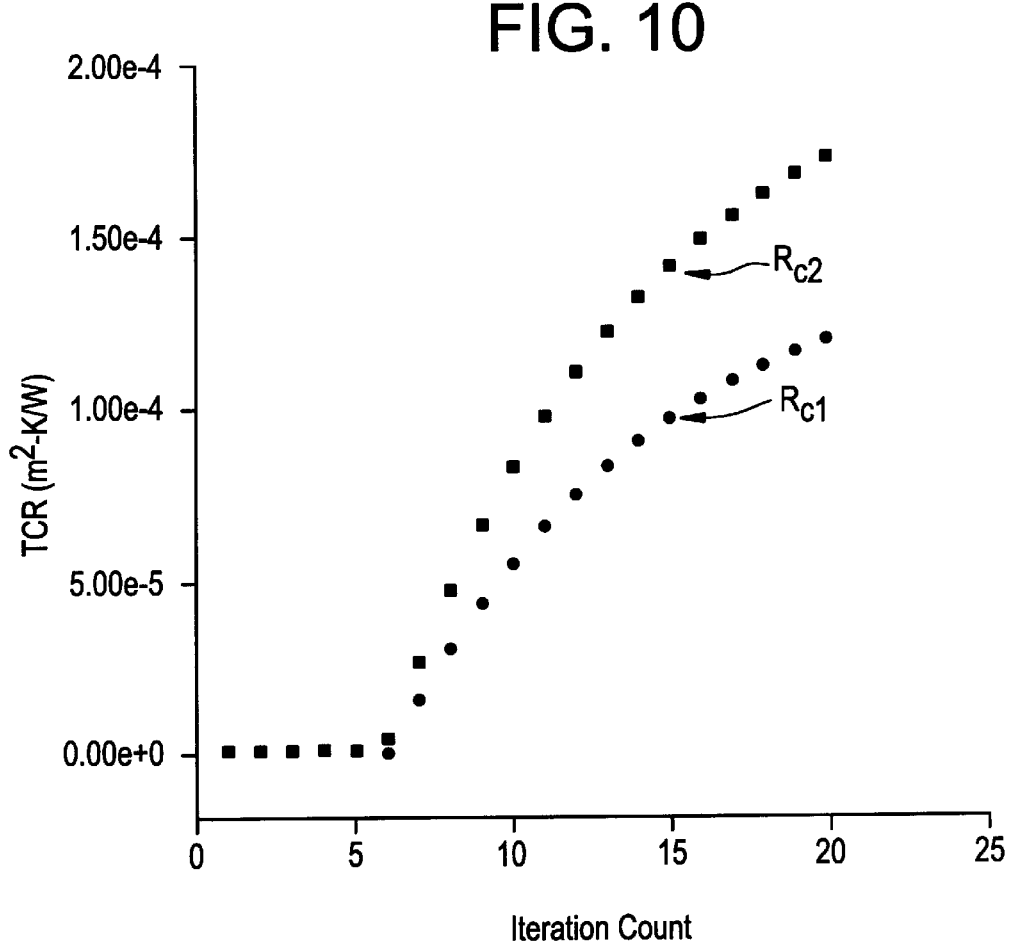
FIG. 10 is a graph of the determination of the thermal contact resistance of two surfaces of a polystyrene sample using a simulation of an apparatus and method of the present invention.

FIGS. 9 and 10 shown the results determining the thermal conductivity and thermal contact resistance using an apparatus and method of the present invention. The inverse procedure was started with a guess value for the initial value of $\beta$, in this case [0.1, 0.00005, 0.0001]. FIG. 9 shows the values of thermal conductivity component of the parameter vector as it converges to the correct value. At the end of 20 iterations the comported value of k is 0.1744 compared to the actual value of 0.17. Furthermore, the procedure correctly identified the two different TCR values at the two interfaces as seen in FIG. 10. Hence, there appears to be no need to make the assumption that the two interfaces have the same TCR value as has been made by Jurkowski et al. (1989), and also implied in a steady state procedure. It should, thus, be possible to study two different interfaces in a single experiment, and simultaneously determine the thermal contact resistance of each interface using the apparatus and method of the present invention.

Figure 11:
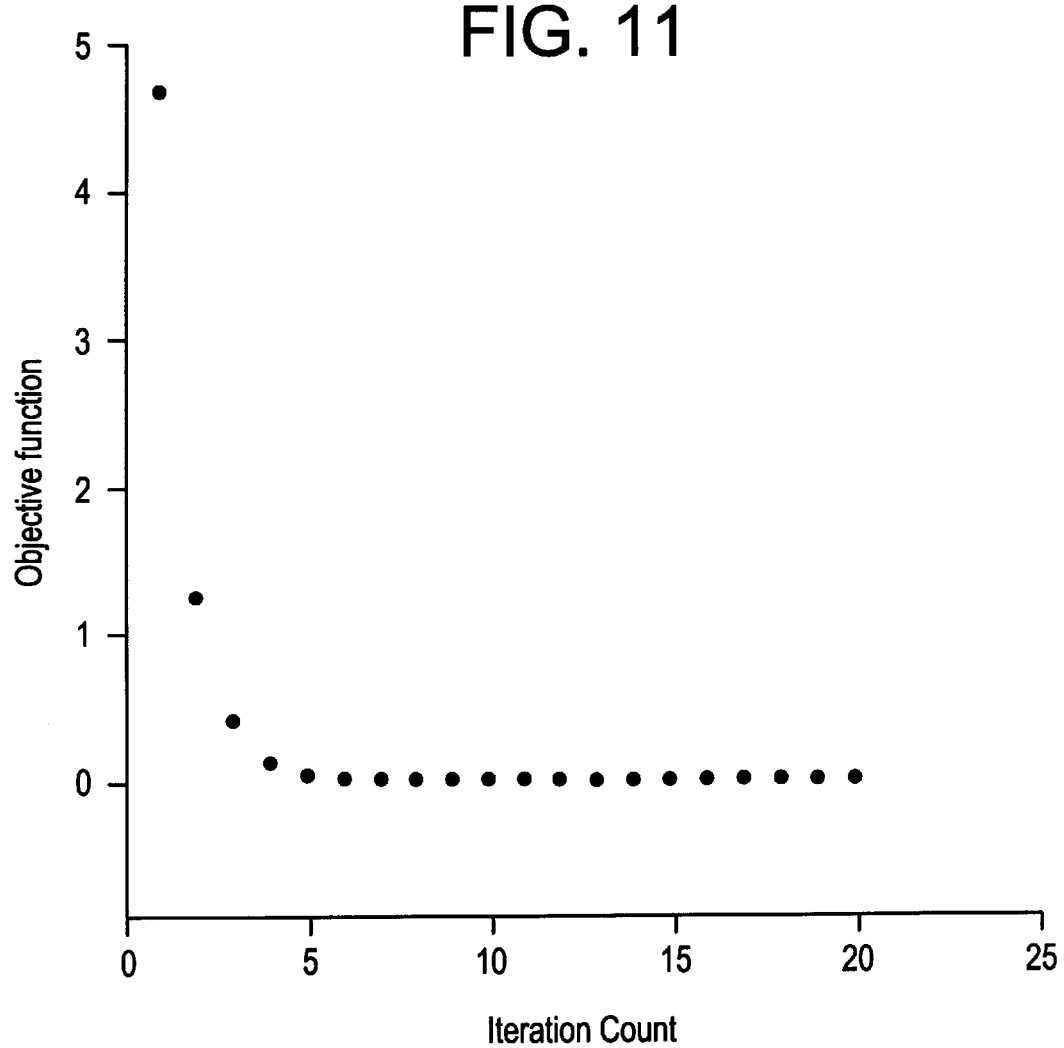
FIG. 11 is a graph of the minimization of the objective function as a check to confirm convergence to solution.

It is possible to approach the correct values of $\beta$ more closely if the iterations are continued further. The simulations showed that the speed of convergence depended to some extent on the total simulation time and the temperature gradients at the two boundaries. Another factor which needed to be adjusted by trial and error was the interval $\delta\beta$, used to compute the sensitivity by a first order finite difference formula. FIG. 11 shows the value of the objective function $S(\beta)$, which initially decreases rapidly. The value of S is used as a check to confirm that the procedure is converging to the solution. In a few cases, particularly when the guesses were not close enough to the correct value of S did not decrease within the next two iterations because previous tests showed that if the increase in S continued for more than two iterations the computed result would not converge to the solution. This is one of the drawbacks of the Gauss method, and Dulikravich and Martin (1997) have presented some hybrid strategies which can be used to overcome this defect. However, in the present study, where the range of k and TCR values are approximately known, the Gauss method was felt to be adequate.

Finally, the effect of the location of the measured temperature vector node was studied by varying the location from the interface node to a node located at a distance of 0.0012 m form the interface. In this range, the location of this node did not affect the convergence. This range represents a typical location of the thermocouple nearest to the interface in the contact resistance measurements.

CONCLUSION

Thermal contact resistance at the plastic-metal interface during injection molding appears to be a time-dependent phenomenon. Therefore, TCR values measured from steady state conduction experiments are unlikely to provide correct TCR data for use in the simulation of the cooling process. Direct methods are not available for measuring TCR from transient heat conduction experiments. Therefore, the apparatus and method of the present invention, is proposed for measuring time-dependent TCR and determining values that are more accurate and precise than those determined using the steady state method.

REFERENCES

Beck, J. V., and Arnold, K. J. (1974). *Parameter Estimation in Engineering and Science,* John Wiley, New York.
Dulikravich, G. S., and Martin, T. J. (1997). *Inverse Problems and Optimization in Heat Conduction,* Taylor and Francis, Washington, D.C.
Fletcher, L. S. (1988). "Recent Developments in Contact Conductance Heat Transfer." *Journal of Heat Transfer,* 110:1059–1080.
Holman, J. P., and Gadja, W. J. (1984). *Experimental Methods for Engineers,* McGraw Hill, New York.
Jurkowski, T., Jarny, Y., and Delaunay, D. "Simultaneous Identification of Thermal Conductivity and Thermal Contact Resistance Without Internal Temperature Measurements." *ICHEME Symposium Series No. 129.*
Lobo, H., and Cohen, C. (1990). "Measurement of Thermal Conductivity of Polymer Melts by the Line Source Method." *Polymer Engg. and Sc.,* 30(2), 65–69.
Lobo, H., and Newman, R. (1990). "Thermal Conductivity of Polymers at High Temperatures and Pressures." *SPE-ANTEC '90,* 862–865.
Mohr, J. W., Seyed-Yagoobi, J., and Price, D. C. (1997). "Thermal Contact Conductance at a Paper/Elastomer Interface." *Journal of Heat Transfer,* 119:363–366.
Moses, W. M., and Johnson, R. R. (1989). "Experimental Results for the Quasisteady Heat Transfer Through Periodically Contacting Surfaces." *J. Thermophysics,* 3(4):474–476.
Narh, K. A., and Sridhar, L. "Measurement and Modeling of Thermal Contact Resistance at a Plastic Metal Interface." *ANTEC '97,* Toronto, Canada, 2273–2277.
Peterson, G. P., and Fletcher, L. S. (1988). "Evaluation of Thermal Contact Conductance Between Mold Compound and Heat Spreader Material." *Journal of Heat Transfer,* 110:996–999.
Rhee, B. O., Hieber, C. A., and Wang, K.K. "Experimental Investigation of Thermal Contact Resistance in Injected Molding." *SPE-ANTEC '93.*
Yu, C. J., Sunderland, J. E., and Poli, C. (1990). "Thermal Contact Resistance in Injection Molding." *Polymer Engineering and Science,* 30(24):1599–1605.

Many other variations and modifications of the invention will be apparent to those skilled in the art without departing from the spirit and scope of the invention. The above described Example and detailed description are, therefore, intended to be merely exemplary, and all such variations and modifications are intended to be included with the scope of the invention.

Furthermore, various publications are cited herein, the disclosures of which are incorporated by reference in their entireties.

What is claimed is:

1. Apparatus for simultaneously determining thermal conductivity and thermal contact resistance of a sample, wherein said sample defines a first and second surface, and said apparatus comprises:

a) a first block comprising an upper surface, a lower surface, and a periphery, wherein the melting point of said first block is greater than the melting point of said sample;

b) a second block comprising an upper surface, a lower surface, and a periphery, wherein the melting point of said second block is greater than the melting point of said sample;

c) a sample chamber for holding said sample, wherein said chamber is defined by said lower surface of second block and said upper surface of said first block, such that a first interface is formed between said first surface of said sample and said lower surface of said second block, and a second interface is formed between said second surface of said sample and said upper surface of said first block;

d) means for modulating the temperature of said sample in said chamber;

e) means for measuring the temperature of said first block and said second block as a function of time while said temperature of said sample is modulated; and f) a computing means interfaced with said temperature measuring means, wherein said computing means simultaneously determines the thermal conductivity of said sample and the thermal contact resistance of said sample at said first and second interfaces with the temperatures of said first block and said second block as a function of time, wherein said computing means utilizes the function:

$$\beta_{k+1}=\beta_k+[X^TWX+V]^{-1}[X^TW(T-\eta(\beta_k))+V(v-\beta_k)],$$

where:

C is heat capacity (J/m$^3$–K), k is thermal conductivity (W/m–K),

R$_c$ is thermal contact resistance (m$^2$–K/W), n,m are number of points at which k and R$_c$ are defined, respectively, t is time (seconds), T is Temperature, vector of measured temperature (C.), V is variance matrix, W is weighting matrix, x is axial distance (m), X is sensitivity matrix=[$\partial\eta_i/\partial\eta\beta_j$], β is parameter vector=[k$_{t=1,n}$ R$_{c1}|_{t=1,n}$ R$_{c2}|_{t=1,n}$]$^T$, η is Temperature, vector of temperatures from physical model of apparatus (°C.), v is initial value of β, $R_s$ is the thermal resistance of the sample=$t/kA(m^2-K/W)$, $t_h$ is sample thickness (m), A is surface area (m²), subscripts 1,2 are upper and lower interfaces between plastic specimen and steel blocks, respectively.

2. The apparatus of claim 1, wherein said first and second blocks are comprised of a material that conducts heat.

3. The apparatus of claim 2, wherein said material comprises copper, steel, gold, aluminum, or TEFLON.

4. The apparatus of claim 3, wherein said first and second blocks are cylindrically shaped and comprised of mold steel.

5. The apparatus of claim 1, wherein said means of modulating the temperature of said sample comprises a heat source connected to said upper surface of said second block, and a heat sink connected to said lower surface of said first block, such that said heat sink has a temperature less than the temperature of said heat source, and heat propagates in a one dimensional direction from said heat source to said heat sink.

6. The apparatus of claim 5, wherein said heat source comprises a beam of electromagnetic radiation focused onto said upper surface of said second block, combustion of an inflammable material at said upper surface of said second block, or an electrical heater which undergoes joule heating.

7. The apparatus of claim 6, wherein said heat source comprises an electrical heater which undergoes joule heating, wherein said electrical heater is connected to said upper surface of said second block.

8. The apparatus of claim 5, wherein said heat sink comprises a coiled metal tube contained in a copper jacket, wherein said tube contains a constant temperature bath of circulating heat transfer oil.

9. The apparatus of claim 1, wherein said means of modulating the temperature of said sample comprises a heat source connected to said lower surface of said first block, and a heat sink connected to said upper surface of said second block, such that said heat sink has a temperature less than the temperature of said heat source, and heat produced from said heat sources propagates in a one dimensional direct from said heat source to said heat sink.

10. The apparatus of claim 9, wherein said heat source comprises a beam of electromagnetic radiation focused onto said lower surface of said first block, combustion of an inflammable material at said lower surface of said first block, or an electrical heater which undergoes joule heating connected to said lower surface of said first block.

11. The apparatus of claim 10, wherein said heat source comprises an electrical heater which undergoes joule heating connected to said lower surface of said first block.

12. The apparatus of claim 9, wherein said heat sink comprises a coiled metal tube contained in a copper jacket, wherein said tube contains a constant temperature bath of circulating heat transfer oil.

13. The apparatus of claim 1, wherein said temperature measuring means comprises a temperature sensing means connected to said blocks, and a temperature calculating means connected to said temperature sensing means, wherein said temperature calculating means converts a signal from said temperature sensing means into a numerical temperature value.

14. The apparatus of claim 13, wherein said temperature sensing means comprises a thermometer, a thermocouple or a fiber optic fluorescence based temperature sensor connected to said first and second blocks.

15. The apparatus of claim 13, wherein said temperature calculating means comprises a computer having a data acquisition system comprising an isothermal terminal block, multiplexer/signal conditioner and data acquisition board, for converting signals received from said temperature sensing means into a numerical temperature value.

16. The apparatus of claim 13, wherein said first and second blocks each comprise at least a single bore, wherein said bores extend from said periphery of said blocks to a central axis of said blocks, are perpendicular to said periphery, are parallel to said upper and lower surfaces of said blocks, and are located at specific nodes relative to said first and second interfaces of said sample in said sample chamber, and said temperature sensing means is inserted into said bores and contacts said blocks at said central axes.

17. The apparatus of claim 16, wherein said temperature sensing means comprises a J-type thermocouple inserted into said bores, such that the tip of said thermocouple in each bore contacts said respective block at said central axis, and said temperature calculating means comprises a computer connected to said thermocouples, wherein said computer comprises a data acquisition system comprising an isothermal terminal block, multiplexer/signal conditioner and data acquisition board, for converting signals received from said temperature sensing means into a numerical temperature value.

18. The apparatus of claim 1, wherein said computing means comprises a computer programmed to solve the function $$\beta_{k+1}=\beta_k+[X^TWX+V]^{-1}[X^TW(T-\eta(\beta_k))+V(v-\beta_k)].$$

19. The apparatus of claim 1, further comprising a pressure modulating means for modulating the pressure under which said sample is held in said sample chamber.

20. The apparatus of claim 19, wherein said pressure modulating means comprises a means of translating said second block towards to said first block such that said lower surface of said second block remains parallel to said upper surface of said first block.

21. The apparatus of claim 20, wherein said translating means comprises:

a frame comprising an upper plate having an internally threaded bore, and a lower plate connected to at least two guide rods perpendicular to said lower plate, wherein said guide rods are positioned such that said first block, said second block, said sample chamber and said temperature modulating means are located between said guide rods;

a plate connected to said upper surface of said second block, wherein said plate comprises at least two holes so that said guide rods can pass through said plate; and an externally threaded rotatable shaft having an upper end and a lower end, wherein shaft engages said internally threaded bore, and said lower end of said shaft is in contact with said plate, such that when said shaft is rotated, said second block is translated towards said first block, the volume of said sample chamber decreases, and pressure upon said sample in said sample chamber increases.

22. Apparatus for simultaneously determining the thermal conductivity and thermal contact resistance of a sample, wherein said sample defines a first and second surface, and said apparatus comprises:

a) a first block comprising an upper surface, a lower surface, and a periphery, wherein said first block comprises a melting point greater than the melting point of said sample;

b) a second block comprising an upper surface, a lower surface, and a periphery, wherein said second block comprises a melting point greater than the melting point of said sample;

c) a sample chamber for holding said sample, wherein said chamber is defined by said lower surface of second block and said upper surface of said first block, such that a first interface is formed between said first surface of said sample and said lower surface of said second block, and a second interface is formed between said second surface of said sample and said upper surface of said first block;

d) a heat source connected to said upper surface of said second block;

e) a heat sink connected to said lower surface of said first block, wherein said heat sink has a temperature less than that of said heat source, wherein said heat source and said heat sink modulate the temperature of said sample;

f) temperature sensing means connected to said blocks;

g) a temperature calculating means connected to said temperature sensing means, wherein said temperature calculating means converts a signal from said temperature sensing means into a numerical temperature value; and h) a computing means interfaced with said temperature calculating means, wherein said computing means simultaneously determines the thermal conductivity of said sample and the thermal contact resistance of said sample at said first and second interfaces with the temperatures of said first block and said second block as a function of time, wherein said computing means utilizes the function:

$$\beta_{k+1} = \beta_k + [X^T W X + V]^{-1} [X^T W (T - \eta(\beta_k)) + V(\nu - \beta_k)]$$

where:

C is heat capacity ($j/m^3$-K), k is thermal conductivity (W/m-K), $R_c$ is thermal contact resistance ($m^2$-K/W), n,m are number of points at which k and $R_c$ are defined, respectively, t is time (seconds), T is Temperature, vector of measured temperature (C.), V is variance matrix, W is weighting matrix, X is axial distance (m), x is sensitivity matrix=$[\partial \eta_i / \partial \beta_j]$, β is parameter vector=$[k_{t=1,n} \ R_{c1}|_{t=1,n} \ R_{c2}|_{t=1,n}]^T$, η is Temperature, vector of temperatures from physical model of apparatus (°C.), ν is initial value of β, $R_S$ is the thermal resistance of the sample=$t/kA(m^2$-K/W), $t_h$ is sample thickness (m), A is surface area ($m^2$), subscripts 1,2 are upper and lower interfaces between plastic specimen and steel blocks, respectively.

23. The apparatus of claim 22, wherein said first and second blocks are comprised of a material that conducts heat.

24. The apparatus of claim 23, wherein said material comprises copper, steel, iron, gold, aluminum, or TEFLON.

25. The apparatus of claim 22, wherein said first and second blocks are cylindrically shaped and comprised of mold steel.

26. The apparatus of claim 22, wherein said heat source comprises a beam of electromagnetic radiation focused onto said upper surface of said second block, combustion of an inflammable material at said upper surface of said second block, or an electrical heater which undergoes joule heating, and is connected to said upper surface of said second block.

27. The apparatus of claim 26, wherein said heat source comprises an electrical heater which undergoes joule heating.

28. The apparatus of claim 22, wherein said temperature sensing means comprises a thermometer, a thermocouple or a fiber optic fluorescence based temperature sensor connected to said first and second blocks.

29. The apparatus of claim 22, wherein said temperature calculating means comprises a computer having a data acquisition system comprising an isothermal terminal block, multiplexer/signal conditioner and data acquisition board, for converting signals received from said temperature sensing means into a numerical temperature value.

30. The apparatus of claim 22, wherein said first and second blocks each comprise at least a single bore, wherein said bores extend from said periphery of said blocks to a central axis of said blocks, are perpendicular to said periphery of said blocks, parallel to said upper and lower surfaces of said blocks, and are located at specific nodes from said first and second interfaces of said sample in said sample chamber, and said temperature sensing means is inserted into said bores and contacts said blocks at said central axes.

31. The apparatus of claim 30, wherein said temperature sensing means comprises a J-type thermocouple inserted into said bores, such that the tip of said thermocouple in each bore contacts said respective block at said central axis, and said temperature calculating means connected to said J-type thermocouples comprises a computer having a data acquisition system comprising an isothermal terminal block, multiplexer/signal conditioner and data acquisition board, for converting signals received from said J-type thermocouples into a numerical temperature value.

32. The apparatus of claim 22, wherein said computing means comprises a computer programmed to solve the function $$\beta_{k+1} = \beta_k + [X^T W X + V]^{-1} [X^T W (T - \eta(\beta_k)) + V(\nu - \beta_k)].$$

33. The apparatus of claim 22, wherein said heat sink comprises a coiled metal tube contained in a copper jacket, wherein said tube contains a constant temperature bath of circulating heat transfer oil.

34. The apparatus of claim 22, further comprising a pressure modulating means for modulating the pressure under which said sample is held in said sample chamber.

35. The apparatus of claim 34, wherein said pressure modulating means comprises a means of translating said second block towards said first block such that said lower surface of said second block remains parallel to said upper surface of said first block.

36. The apparatus of claim 34, wherein said translating means comprises:

a frame comprising an upper plate having an internally threaded bore, and a lower plate connected to at least two guide rods which are perpendicular to said lower plate, wherein said guide rods are positioned such that said heat sink, said first block, said second block and said heat source are located between said guide rods;

a plate connected to said heat source such that said heat source is located between said plate and said second block, wherein said plate comprises at least two holes so that said guide rods can pass through said plate; and an externally threaded rotatable shaft having an upper end and a lower end, wherein shaft engages said internally threaded bore, and said lower end of said shaft is in contact with said plate, such that when said shaft is rotated, said second block is translated towards said first block, the volume of said sample chamber decreases, and pressure upon said sample in said sample chamber increases.

37. A method for simultaneously determining the thermal conductivity and thermal contact resistance of a sample, wherein the sample defines a first and second surface, wherein the method comprises the steps of:
   a) providing a first block comprising an upper surface, a lower surface and a periphery, and a second block comprising an upper surface, a lower surface, and a periphery, wherein the first and second blocks comprise melting points greater than the melting point of the sample;
   b) forming a sample chamber for holding the sample by positioning the first and second blocks such that the upper surface of the first block is parallel to the lower surface of the second block;
   c) placing the sample in the sample chamber so that a first interface is formed between the first surface of the sample and the lower surface of the second block, and a second interface is formed between the second surface of the sample and the upper surface of the first block;
   d) modulating the temperature of the sample;
   e) measuring the temperature of the first and second blocks at specific nodes relative to the first and second interfaces as a function of time during the modulating of the temperature of the sample; and
   f) determining simultaneously the thermal conductivity of the sample, and the thermal contact resistance of the sample at the first and second interfaces, using the function:

$$\beta_{k+1}=\beta_k+[X^TWX+V]^{-1}[X^TW(T-\eta(\beta_k))+V(v-\beta_k)],$$

where:

C is heat capacity ($j/m^3$-K),
k is thermal conductivity (W/m-K),
$R_c$ is thermal contact resistance ($m^2$-K/W),
n,m are number of points at which k and $R_c$ are defined, respectively,
t is time (seconds),
T is Temperature, vector of measured temperature (C.),
V is variance matrix,
W is weighting matrix,
x is axial distance (m),
X is sensitivity matrix=$[\partial\eta_i/\partial\beta_j]$,
$\beta$ is parameter vector=$[k_{t=1,n}\ R_{c1}|_{t=1,n}\ R_{c2}|_{t=1,n}]^T$,
$\eta$ is Temperature, vector of temperatures from physical model of apparatus (°C.),
v is initial value of $\beta$,
$R_S$ is the thermal resistance of the sample=t/kA($m^2$-K/W),
$t_h$ is sample thickness (m),
A is surface area ($m^2$), subscripts
   1,2 are upper and lower interfaces between plastic specimen and steel blocks, respectively.

38. The method of claim 37, wherein the step of determining simultaneously the thermal conductivity of the sample and the thermal contact resistance of the sample at the first and second interfaces, comprises programming a computer to solve the function:

$$\beta_{k+1}=62_k+[X^TWX+V]^{-1}[X^TW(T-\eta(\beta_k))+V(v-\beta_k)].$$

39. The method of claim 37, wherein the first and second blocks are comprised of a material that conducts heat.

40. The method of claim 39, wherein the material comprises copper, iron, steel, gold, aluminum, or TEFLON.

41. The method of claim 40, wherein the first and second blocks are cylindrically shaped and comprised of mold steel.

42. The method of claim 37, wherein the step of modulating the temperature of the sample comprises connecting a heat source to the upper surface of the second block, and connecting a heat sink to the lower surface of the first block so that the temperature of the heat sink is less than the temperature of the heat source, and heat produced by the heat source is conducted through the sample in the sample chamber to the heat sink in a one dimensional direction.

43. The method of claim 42, wherein the heat source comprises an electrical heater, a beam of electromagnetic radiation focused onto the upper surface of the second block, or combustion of an inflammable material at the upper surface of the second block.

44. The method of claim 43, wherein the heat source comprises an electrical heater connected to the upper surface of the second block.

45. The method of claim 42, wherein the heat sink comprises a coiled metal tube contained in a copper jacket, wherein the tube is located in a constant temperature bath of circulating heat transfer oil.

46. The method of claim 37, wherein the step of modulating the temperature of the sample comprises connecting a heat source to the lower surface of the first block, and a heat sink to the upper surface of the second block so that the heat sink has a temperature less than the temperature of the heat source, and heat generated by the heat source is conducted through the sample in the sample chamber, to the heat sink in a one dimensional direction.

47. The method of claim 46, wherein the heat source comprises an electrical heater, a beam of electromagnetic radiation focused onto the upper surface of the second block, or an combustion of an inflammable material at the lower surface of the first block.

48. The method of claim 47, wherein the heat source comprises an electrical heater connected to the lower surface of the first block.

49. The method of claim 46, wherein the heat sink connected to the upper surface of the second block comprises a coiled metal tube contained in a copper jacket, wherein the tube contains a constant temperature bath of circulating heat transfer oil.

50. The method of claim 37, wherein the temperature measuring step comprises connecting a temperature sensing means to the blocks, and connecting a temperature calculating means to the temperature sensing means, wherein the temperature calculating means converts a signal from the temperature sensing means into a numerical temperature value.

51. The method of claim 50, wherein the temperature sensing means comprises a thermometer, a thermocouple, or a fiber optic fluorescence based temperature sensor.

52. The method of claim 50, wherein the temperature calculating means comprises a computer having a data acquisition system comprising an isothermal terminal block, multiplexer/signal conditioner and data acquisition board, for converting signals received from the temperature sensing means into a numerical temperature value.

53. The method of claim 50, wherein the first and second blocks each comprise at least a single bore that extend from the periphery of the blocks to a central axis of the blocks, wherein the bores are perpendicular to the periphery of the blocks, parallel to the upper and lower surfaces of the blocks, and are located at specific nodes relative to the first and second interfaces of the sample in the sample chamber, and the temperature sensing means is inserted into the bores and contacts the blocks at the central axes.

54. The method of claim 53, wherein the temperature sensing means comprises a J-type thermocouple inserted into the bores, such that the tip of the thermocouple in each bore contacts the respective block at the central axis, and the temperature calculating means comprises a computer connected to the thermocouples, wherein the computer comprises a data acquisition system comprising an isothermal terminal block, multiplexer/signal conditioner and data acquisition board, for converting signals received from the temperature sensing means into a numerical temperature value.

55. The method of claim 37, further comprising the step of modulating the pressure under which the sample is held in the sample chamber, and maintaining the modulated pressure prior to modulating the temperature of the sample.

56. The method of claim 55, wherein the pressure modulating step comprises a translating the second block towards to the first block such that the lower surface of the second block remains parallel to the upper surface of the first block.

57. The method of claim 56, wherein the step of translating the second block comprises:

providing a frame comprising an upper plate having an internally threaded bore, and a lower plate connected to at least two guide rods which are perpendicular to said lower plate, wherein the guide rods are positioned such that the first block, the second block, the sample chamber are located between the guide rods;

connecting a plate to the upper surface of the second block, wherein the plate comprises at least two holes aligned with the guide rods so that the guide rods can pass through said plate;

providing an externally threaded rotatable shaft having an upper end and a lower end, wherein the shaft engages the internally threaded bore, and the lower end of the shaft is in contact with said plate; and rotating the shaft so that the second block is translated towards the first block, the volume of the sample chamber decreases, and pressure upon the sample in the sample chamber increases.

\* \* \* \* \*